United States Patent
Bansal

(10) Patent No.: US 9,243,070 B2
(45) Date of Patent: Jan. 26, 2016

(54) HUMANIZED AND CHIMERIC ANTI-FACTOR BB ANTIBODIES AND USES THEREOF

(71) Applicant: NovelMed Therapeutics, Inc., Cleveland, OH (US)

(72) Inventor: Rekha Bansal, Twinsburg, OH (US)

(73) Assignee: Novelmed Therapeutics, Inc., Cleveland, OH (US)

( * ) Notice: Subject to any disclaimer, the term of this patent is extended or adjusted under 35 U.S.C. 154(b) by 0 days.

(21) Appl. No.: 14/390,632

(22) PCT Filed: Apr. 2, 2013

(86) PCT No.: PCT/US2013/034982
§ 371 (c)(1),
(2) Date: Oct. 3, 2014

(87) PCT Pub. No.: WO2013/152020
PCT Pub. Date: Oct. 10, 2013

(65) Prior Publication Data
US 2015/0093390 A1 Apr. 2, 2015

Related U.S. Application Data

(60) Provisional application No. 61/619,858, filed on Apr. 3, 2012.

(51) Int. Cl.
*A61K 39/395* (2006.01)
*C07K 16/36* (2006.01)
*C07K 16/40* (2006.01)
*C07K 16/18* (2006.01)
*A61K 39/00* (2006.01)

(52) U.S. Cl.
CPC ............... *C07K 16/40* (2013.01); *C07K 16/18* (2013.01); *A61K 2039/505* (2013.01); *C07K 2317/24* (2013.01); *C07K 2317/34* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,679,546 | A | 10/1997 | Ko | |
|---|---|---|---|---|
| 8,981,060 | B2 * | 3/2015 | Bansal | 530/387.1 |
| 2005/0107319 | A1 | 5/2005 | Bansal | |
| 2008/0075720 | A1 | 3/2008 | Holers et al. | |
| 2008/0299114 | A1 | 12/2008 | Emlem et al. | |
| 2010/0239573 | A1 * | 9/2010 | Bansal | 424/133.1 |
| 2013/0039925 | A1 | 2/2013 | Bansal | |

FOREIGN PATENT DOCUMENTS

| WO | 2007056227 A2 | 5/2007 |
|---|---|---|
| WO | 2008140653 A2 | 11/2008 |
| WO | 2009029669 A1 | 3/2009 |

OTHER PUBLICATIONS

Rudikoff et al., Proc Natl Acad Sci USA 79: 1979-1983, 1982.*
Colman, Research in Immunology 145: 33-36, 1994.*
Kussie et al., J. Immunol. 152: 146-152, 1994.*
Chen et al., EMBO J., 14: 2784-2794, 1995.*
Leinhase, Iris, et al., "inhibition of the alternative complement activation pathway in traumatic brain injury by a monoclonal anti-factor B antibody: a randomized placebo-controlled study in mice", Journal of Neuroinflammation, May 2, 2007, vol. 4, No. 13, pp. 1-12.
European Search Report dated Oct. 7, 2015.

* cited by examiner

*Primary Examiner* — Phillip Gambel
(74) *Attorney, Agent, or Firm* — Tarolli, Sundheim, Covell & Tummino LLP

(57) ABSTRACT

A method of inhibiting complement activation mediated by Bb inhibitors in a subject includes administering a Bb inhibitor to the subject to inhibit at least one of Bb binding to factors B and properdin, inhibit C3 cleavage, inhibit the activation of neutrophils, monocytes, platelets, and endothelium; or inhibit the formation of C3a, C5a, and MAC.

17 Claims, 18 Drawing Sheets

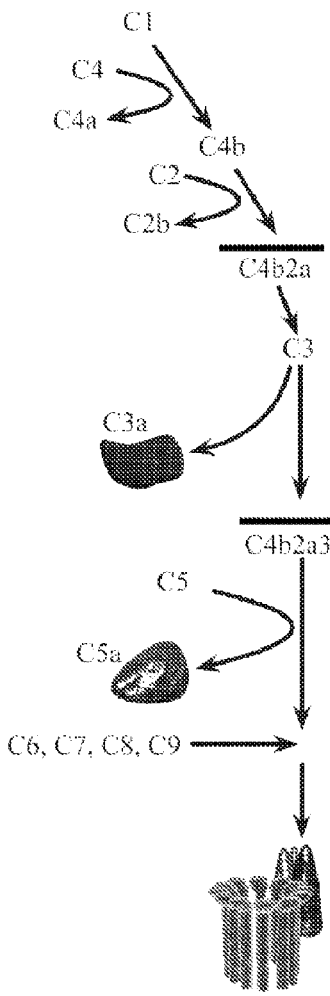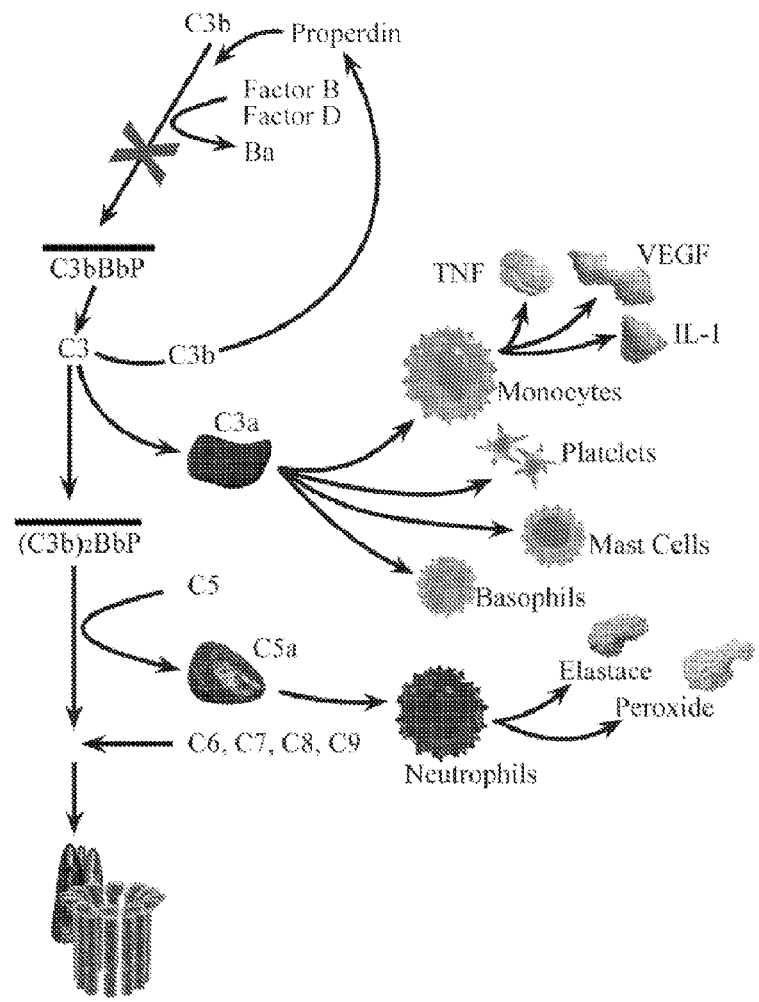
Fig. 1

Amino Acid Sequence of Anti-Bb Antibody

- Anti-Bb-Murine Antibody-HC, SEQ ID No: 1:
QVQLQQSGAELAKPGASVRMSCKASGYTFTNYWIHWVKQRPGQGLEWIGYINPNTGYNDYNQKFKDKATLTADKSSSTVYMQLSSLTSEDSAVYYCARGGQLGLRRAMDYWGQGTSVTVSS

- Anti-Bb-Murine Antibody-LC, SEQ ID No: 2:
DVQITQSPSYLAASPGETITINCRASKSISKYLAWYQDKPGKTNKLLIYSGSTLQSGIPSRFSGSGSGTDFTLTISSLEPEDFAMYYCQQHDEYPWTFGGGTKLEIKRADAAP

- Anti-Bb-Bik-Fab'-Hum03-HC, SEQ ID No: 3:
EVQLVQSGAEVKKPGESLRISCKGSGYTFTNYWIHWIRQSPSRGLEWLGYINPNTGYNDYNQKFKDRVTISADKSISTAYLQWSSLKASDTAMYYCARGGQLGLRRAMDYWGQGTLVTVSS

- Anti-Bb-Bik-Fab'-Hum03-LC, SEQ ID No: 4:
DIQMTQSPSSLSASVGDRVTITCRASKSISKYLAWYQQKPGKAPKLLIYSGSTLQSGVPSRFSGSGSGTEFTLTISSLQSEDFAVVYCQQHDEYPWTFGQGTKVEIKRTVA

- Anti-Bb-Bik-Fab'-Ha-HC, SEQ ID No: 5:
EVQLVESGGGLVQPGRSLRLSCAASGYTFTNYWIHWVRQAPGKGLEWVSYINPNTGYNDYNQKFKDRFTISRDNAKNSLYLQMNSLRAEDTAVYYCAKGGQLGLRRAMDYWGQGTLVTVSS

- Anti-Bb-Bik-Fab'-Ha-LC, SEQ ID No: 6:
DIQMTQSPSSLSASVGDRVTITCRASKSISKYLAWYQQKPGKAPKLLIYSGSTLQSGVPSRFSGSGSGTDFTLTISSLQPEDVATYYCQQHDEYPWTFGQGTKVEIKRTVA

- Anti-Bb-Bik-Fab'-An-HC, SEQ ID No: 7:
EVQLVESGGGLVQPGGSLRLSCAASGYTFTNYWIHWVRQAPGKGLEWVGYINPNTGYNDYNQKFKDRFTFSLDTSKSTAYLQMNSLRAEDTAVYYCAKGGQLGLRRAMDYWGQGTLVTVSS

- Anti-Bb-Bik-Fab'-An-LC, SEQ ID No: 8:
DIQMTQSPSSLSASVGDRVTITCRASKSISKYLAWYQQKPGKAPKVLIYSGSTLQSGVPSRFSGSGSGTDFTLTISSLQPEDFATYYCQQHDEYPWTFGQGTKVEIKRTVA

- Anti-Bb-Bik-Fab'-Ea-Humanized Version 1- HC, SEQ ID No: 9:
QVQLVQSGAEVKKPGASVKMSCKASGYTFTNYWIHWVRQAPGQGLEWMGYINPNTGYNDYNQKFKDRATLTADKSSSTVYMQLSSLRSEDTAVYYCARGGQLGLRRAMDYWGQGTLVTVSS

- Anti-Bb-Bik-Fab'-Ea-Humanized Version 1- LC, SEQ ID No: 10:
DVQITQSPSTLSASPGDRITITCRASKSISKYLAWYQDKPGKTNKLLIYSGSTLQSGIPSRFSGSGSGTEFTLTISSLQPDDFAMYYCQQHDEYPWTFGQGTKLEIK

- Anti-Bb-Bik-Fab'-Ea-Humanized Version 2- HC, SEQ ID No: 11:
QVQLVQSGAEVAKPGASVKMSCKASGYTFTNYWIHWVKQRPGQGLEWIGYINPNTGYNDYNQKFKDKATLTADKSSSTVYMQLSSLTSEDTAVYYCARGGQLGLRRAMDYWGQGTLVTVSS

- Anti-Bb-Bik-Fab'-Ea-Humanized Version 2- LC, SEQ ID No: 12:
DVQITQSPSYLSASPGDTITITCRASKSISKYLAWYQDKPGKTNKLLIYSGSTLQSGIPSRFSGSGSGTEFTLTISSLQPDDFAMYYCQQHDEYPWTFGQGTKLEIK

Fig. 12

Amino Acid Sequence of the CDRs and Framework Regions

Anti-Bb-Bik-Fab'-Hum03

Anti-Bb-Bik-Fab'-Hum03-HC

| | |
|---|---|
| SEQ ID NO 13 | EVQLVQSGAEVKKPGESLRISCKGS |
| SEQ ID NO 14 | GYTFTNYWIH |
| SEQ ID NO 15 | WIRQSPSRGLEWLG |
| SEQ ID NO 16 | YINPNTGYNDYNQKFKD |
| SEQ ID NO 17 | RVTISADKSISTAYLQWSSLKASDTAMYYCAR |
| SEQ ID NO 18 | GGQLGLRRAMDY |
| SEQ ID NO 19 | WGQGTLVTVSS |

Anti-Bb-Bik-Fab'-Hum03-LC

| | |
|---|---|
| SEQ ID NO 20 | DIQMTQSPSSLSASVGDRVTITC |
| SEQ ID NO 21 | RASKSISKYLA |
| SEQ ID NO 22 | WYQQKPGKAPKLLIY |
| SEQ ID NO 23 | SGSTLQS |
| SEQ ID NO 24 | GVPSRFSGSGSGTEFTLTISSLQSEDFAVYYC |
| SEQ ID NO 25 | QQHDEYPWT |
| SEQ ID NO 26 | FGQGTKVEIKRTVA |

Fig. 13

Amino Acid Sequence of the Framework Regions

Anti-Bb-Bik-Fab'-Ha

Anti-Bb-Bik-Fab'-Ha-HC

| | |
|---|---|
| SEQ ID NO 27 | EVQLVESGGGLVQPGRSLRLSCAAS |
| SEQ ID NO 28 | WVRQAPGKGLEWVS |
| SEQ ID NO 29 | RFTISRDNAKNSLYLQMNSLRAEDTAVYYCAK |
| SEQ ID NO 19 | WGQGTLVTVSS |

Anti-Bb-Bik-Fab'-Ha-LC

| | |
|---|---|
| SEQ ID NO 20 | DIQMTQSPSSLSASVGDRVTITC |
| SEQ ID NO 22 | WYQQKPGKAPKLLIY |
| SEQ ID NO 30 | GVPSRFSGSGSGTDFTLTISSLQPEDVATYYC |
| SEQ ID NO 26 | FGQGTKVEIKRTVA |

Fig. 14

Amino Acid Sequence of the Framework Regions

Anti-Bb-Bik-Fab'-An

Anti-Bb-Bik-Fab'-An-HC

SEQ ID NO 31    EVQLVESGGGLVQPGGSLRLSCAAS
SEQ ID NO 32    WVRQAPGKGLEWVG
SEQ ID NO 33    RFTFSLDTSKSTAYLQMNSLRAEDTAVYYCAK
SEQ ID NO 19    WGQGTLVTVSS

Anti-Bb-Bik-Fab'-An-LC

SEQ ID NO 20    DIQMTQSPSSLSASVGDRVTITC
SEQ ID NO 34    WYQQKPGKAPKVLIY
SEQ ID NO 35    GVPSRFSGSGSGTDFTLTISSLQPEDFATYYC
SEQ ID NO 26    FGQGTKVEIKRTVA

Fig. 15

Amino Acid Sequence of the Framework Regions

Anti-Bb-Bik-Fab'-Ea-Humanized Version 1

Anti-Bb-Humanized Version 1- HC

SEQ ID NO 36    QVQLVQSGAEVKKPGASVKMSCKAS
SEQ ID NO 37    WVRQAPGQGLEWIG
SEQ ID NO 38    RATLTADKSSSTVYMQLSSLRSEDTAVYYCAR
SEQ ID NO 19    WGQGTLVTVSS

Anti-Bb-Humanized Version 1- LC

SEQ ID NO 39    DVQITQSPSTLSASPGDRITITC
SEQ ID NO 40    WYQQDKPGKTNKLLIY
SEQ ID NO 41    GIPSRFSGSGSGTEFTLTISSLQPDDFAMYYC
SEQ ID NO 42    FGQGTKLEIK

Fig. 16

Amino Acid Sequence of the Framework Regions

Anti-Bb-Bik-Fab'-Ea-Humanized Version 2

Anti-Bb-Humanized Version 2- HC

SEQ ID NO 43  QVQLVQSGAEVAKPGASVKMSCKAS
SEQ ID NO 44  WVKQRPGQGLEWIG
SEQ ID NO 45  KATLTADKSSSTVYMQLSSLTSEDTAVYYCAR
SEQ ID NO 19  WGQGTLVTVSS

Anti-Bb-Humanized Version 2- LC

SEQ ID NO 46  DVQITQSPSYLSASPGDTITITC
SEQ ID NO 40  WYQDKPGKTNKLLIY
SEQ ID NO 41  GIPSRFSGSGSGTEFTLTISSLQPDDFAMYYC
SEQ ID NO 42  FGQGTKLEIK

Fig. 17

Epitope Binding Analysis

SEQ ID NO 47  YADPNTCRGDSGGPLI
SEQ ID NO 48  VHKRSRFIQVGVISWG

SEQ ID NO 49  VWEHRKGTDYHKQPWQ
SEQ ID NO 50  GAVVSEYFVLTAAHCF
SEQ ID NO 51  KRDLEIEVVLFHPNYNI

Fig. 18

HUMANIZED AND CHIMERIC ANTI-FACTOR BB ANTIBODIES AND USES THEREOF

RELATED APPLICATION

This application claims priority from U.S. Provisional Application No. 61/619,858, filed Apr. 3, 2012, the subject matter of which is incorporated herein by reference in its entirety.

GOVERNMENT FUNDING

This invention was made with government support under Grant No. R44HL102890 awarded by The National Institutes of Health. The United States government has certain rights to the invention.

FIELD OF THE INVENTION

The present invention relates to humanized and chimeric antibodies and antigen-binding fragments thereof with reduced effector functions and immunogenicity. The present invention further relates to the use of antibodies for factor B for inhibiting the activity of C3bBb or PC3bBb complexes, which will further inhibit the proteolytic activity of factor B in C3/C5 convertases. The humanized and chimeric monoclonal antibodies of this invention selectively block the binding of factor Bb to the PC3bB complex without inhibiting classical pathway activation. These antibodies do not inhibit the interaction of C3b to factor B and therefore have a unique function. Such antibodies are useful treatments for disease indications where alternative complement pathway plays a pathological role.

BACKGROUND OF THE INVENTION

The complement system is activated via three distinct pathways; the classical pathway, the lectin pathway and the alternative complement pathway (AP). The classical pathway is activated via antigen-antibody complexes. The lectin pathway is a variation of the classical pathway and the alternative pathway is activated by foreign material, artificial surfaces, dead tissues, bacteria, dead yeast cells.

Activation of the classical pathway generates C3a, C4a, C5a and C5b-9 molecules which activates a variety of cells in response to host defense. In pathological conditions, as a result of activation of the alternative pathway, anaphylatoxins C3a, C5a are formed which activate cells and C5b-9 molecules also known as the membrane attack complex (MAC) that damage tissues. Collectively these molecules mediate inflammation via cellular activation and release of inflammatory mediators. In addition to the role of C5b-9 as a lytic pore-forming complex, there is strong evidence that the depositing of sublytic MAC may play an important role in inflammation.

The classical complement pathway is important for host defense against pathogens. The alternative complement pathway is activated in pathological inflammation. Elevated levels of C3a, C5a, and C5b-9 have been found associated with multiple acute and chronic disease conditions. Therefore, inhibition of disease-induced AP activation is important for clinical benefit in the diseases where complement activation plays a role in disease pathology.

In addition to its essential role in immune defense, the complement system contributes to tissue damage in many clinical conditions. The activities included in the complement biochemical cascade present a potential threat to host tissue. An example includes the indiscriminate release of destructive enzymes possibly causing host cell lysis. Thus, there is a pressing need to develop therapeutically effective complement inhibitors to prevent these adverse effects.

In a disease condition where AP activation contributes to disease pathology, elevated levels of C3a, C5a and C5b-9 molecules are found in serum, plasma, blood or other body fluids representative of the disease. Production and inhibition of each of these molecules via different mechanisms is important for diseases. One possible mechanism for inhibiting the formation of the PC3bBb complex is via the use of an anti-Bb antibody. Thus blocking/inhibiting or preventing AP activation via depleting Bb, neutralizing Bb, or inactivating Bb remains an important therapeutic strategy.

The present invention relates to developed humanized and chimeric antibody sequences that are novel and provide targeted binding to factor Bb. The binding of such humanized/chimeric antibodies to factor Bb prevents activity of convertase. Such antibodies also prevent conversion of PC3bB into PC3bBb via binding the factor D cleavage site on factor B of the PC3bB complex. These antibodies do not inhibit properdin binding to C3b. Anti-factor Bb agents that bind Bb and prevent PC3bBb activity and prevent formation of new C3 convertase include, but are not limited to, monoclonal and polyclonal antibodies, chimeric, humanized, fully human, and nano-antibodies, Full length and fragments thereof, including IgG, Fab, Fab', F(ab')$_2$, and IgGs. The antibodies of the present invention inhibit the formation of C3a, C5a, and C5b-9 which drive inflammation and also amplify the AP activation process.

Aptamers, small molecules, and SiRNA can also neutralize Bb binding to the PC3bB complex and prevent production of AP induced production of C3a, C5a, and C5b-9. As a result, cellular activation, inflammation and release of inflammatory mediators are also prevented. Because AP activation is linked to various acute and chronic human diseases, the blockade with anti-Bb agents will also block the inflammation process providing clinical benefit to mammals treated with the anti-Bb monoclonal antibodies.

Complement is one of several factors involved in pathogenesis and could be a significant pathological mechanism that offers an effective point for clinical control. The need for effective complement inhibitory drugs is signified by growing recognition of the importance of complement-mediated tissue injury in a variety of disease states. Despite this, currently there is a complete absence of approved drugs for human use that specifically target and inhibit complement activation.

Factor B plays a key role in the amplification loop of the alternative pathway since it provides the catalytic subunit, Bb, for C3-convertase (PC3bBb). Antibodies that inhibit C3b binding to Ba have been developed but none that inhibit the activity of the Bb. Factor B by itself is a zymogen with no known catalytic activity. After binding to PC3b complex, factor B is cleaved by factor D to release Ba. It has been shown that factor B binds C3b through regions found within each of the Ba and Bb subunits Inhibitors of factor Bb binders should results of selective inhibition of factor B function, thereby preventing formation of C3a, C5a and C5b-9, which are responsible for many deleterious effects.

Based on the results described in this patent application, we developed humanized and chimeric antibodies that bind the catalytic domain of factor B and prevent the activity of the PC3bBb, bind the factor D cleavage site on Bb and prevent the formation of additional PC3bBb molecules. These antibodies do not inhibit C3b binding to factor B as such binding events are shown to be mediated via Ba domain of factor B. This application developed humanized and chimeric anti-Bb specific inhibitors or inhibition methods that (a) will prevent factor B function by blocking PC3bBb activity and/or (b) suppress factor B cleavage that prevents Bb generation. These inhibitors appear to be inactivators of the C3 convertase enzymatic activity without disrupting the factor B interaction with C3b. We have evaluated the inhibitory activity of the anti-factor Bb antibodies for their potential role in blocking the AP activation. These antibodies prevent factor B function both in vitro and in whole blood. Other anti-factor Ba monoclonal antibodies have also been developed and tested in animal models of disease but not part of the current invention. These anti-Ba antibodies prevent factor B binding to C3b and hence block the activation of the complement cascade.

This invention is designed to inhibit the functional activity of Bb and its progressive effects in pathological conditions by use of an anti-Bb antibody.

SUMMARY OF THE INVENTION

The present invention relates to a method of inhibiting Bb dependent complement activation by blocking Bb site on PC3bBb and C3bBb, and limiting factor D mediated factor B cleavage. Antibodies that bind Bb and inhibit only alternative pathway activation without inhibiting the classical pathway are covered under this invention. Factor B dependent complement activation can be inhibited by a factor B inhibitor molecule other than antibody such as aptamer and SiRNA. A factor B inhibitor molecule antibody can comprise a whole or fragmented anti-factor B antibody. The fragmented anti-factor B antibody can be $F_{ab}$, $F_{(ab)2}$, $F_v$, or single chain $F_v$. The anti-factor B antibody may be monoclonal, polyclonal, chimeric, or de-immunized and have the ability to bind factor B and its fragments. The present invention discloses the use of Bb antibodies and not anti-Ba antibodies for the treatment of several inflammatory disorders regulated via complement activation.

In one aspect, the present invention relates to a method of inhibiting the adverse effects of Bb-dependent complement activation in a subject. The method includes administering to the subject an amount of a Bb inhibitory agent effective to inhibit Bb-dependent complement activation. In this context, the phrase "Bb-dependent complement activation" refers to activation of all three complement pathways. In some aspects of the invention, the Bb inhibitory agent is an anti-factor Bb antibody or fragment thereof and, in other aspects, the anti-factor Bb antibody has a reduced effector function. In still other aspects, the Bb inhibitory agent is a Bb inhibitory peptide. The methods, compositions, and medicaments of the invention are useful for inhibiting the adverse effects of Bb-dependent complement activation in vivo in mammalian subjects, including humans suffering from acute or chronic pathological conditions where inappropriate complement activation is involved in disease pathology.

In another aspect, the present invention creates an anti-factor Bb antibody containing various combinations of complementarity determining regions 1 through 3 (CDRs 1 through 3), and framework regions (FR1 through FR4). The CDRs include light and heavy chain combinations. CDR-L1, CDR-L2, CDR-L3, CDR-H1, CDR-H2, CDR-H3 and the framework regions are used for the treatment of the above mentioned disease conditions for which complement plays a role. Antibodies that contain the CDRs in any order within the amino acid sequence of the variable region are covered under this invention. As such, this invention covers the sequences discussed as well as any sequence changes in the CDR or framework regions as long as 90% sequence identity is maintained. Such antibodies bind only the Bb molecule with a stoichiometry ratio of 1:1, which means that by using the antibody, one can evaluate the percent activation in a sample of plasma.

BRIEF DESCRIPTION OF THE DRAWINGS

FIG. 1 illustrates the two complement pathways; the classical and the alternative complement pathways. This illustration separates the two pathways and not the convergence of the two pathways at C3b.

FIG. 12 illustrates the sequence of the murine anti-Bb antibody (SEQ ID NO:1 and SEQ ID NO: 2). Sequences of humanized antibody (SEQ ID NO: 3 through SEQ ID NO:12) are presented.

FIG. 13 through FIG. 17 illustrates Sequence ID NO for CDRs and Framework regions.

FIG. 18 shows the peptide motif in Bb protein responsible for murine and humanized anti-Bb binding.

DETAILED DESCRIPTION OF THE INVENTION

Figure 2:
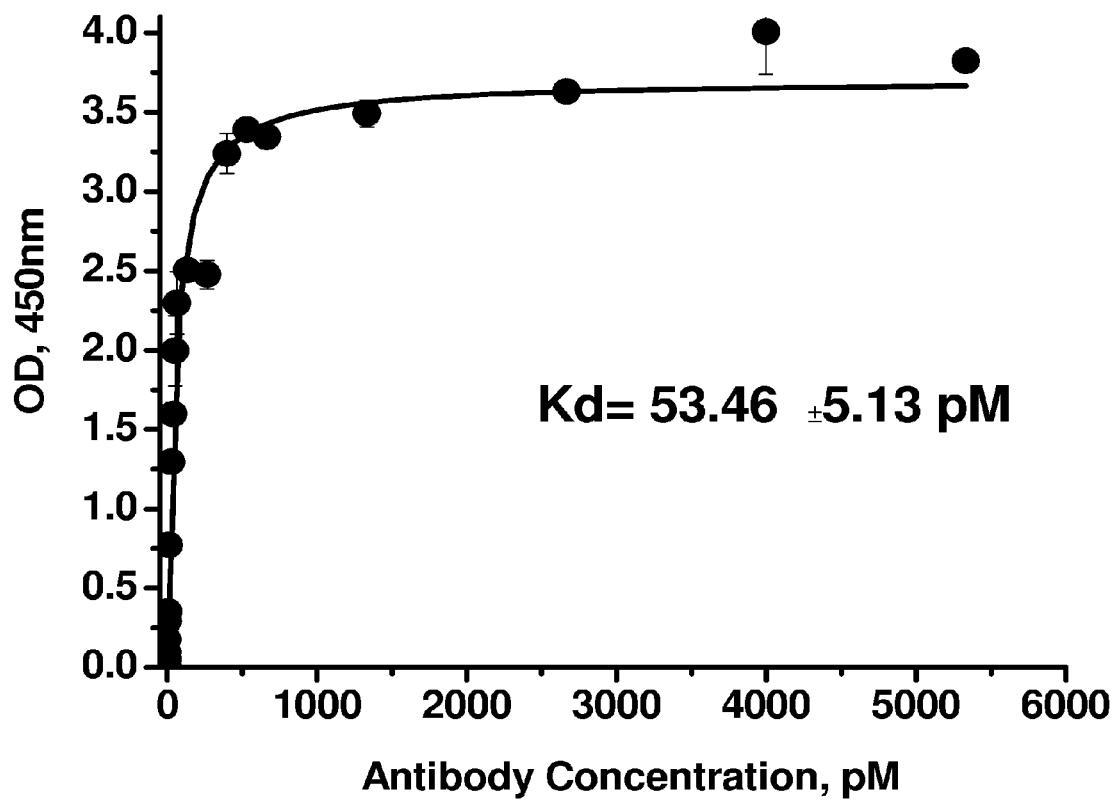
FIG. 2 illustrates the binding affinity of humanized anti-Bb antibody to B protein.
Figure 3:
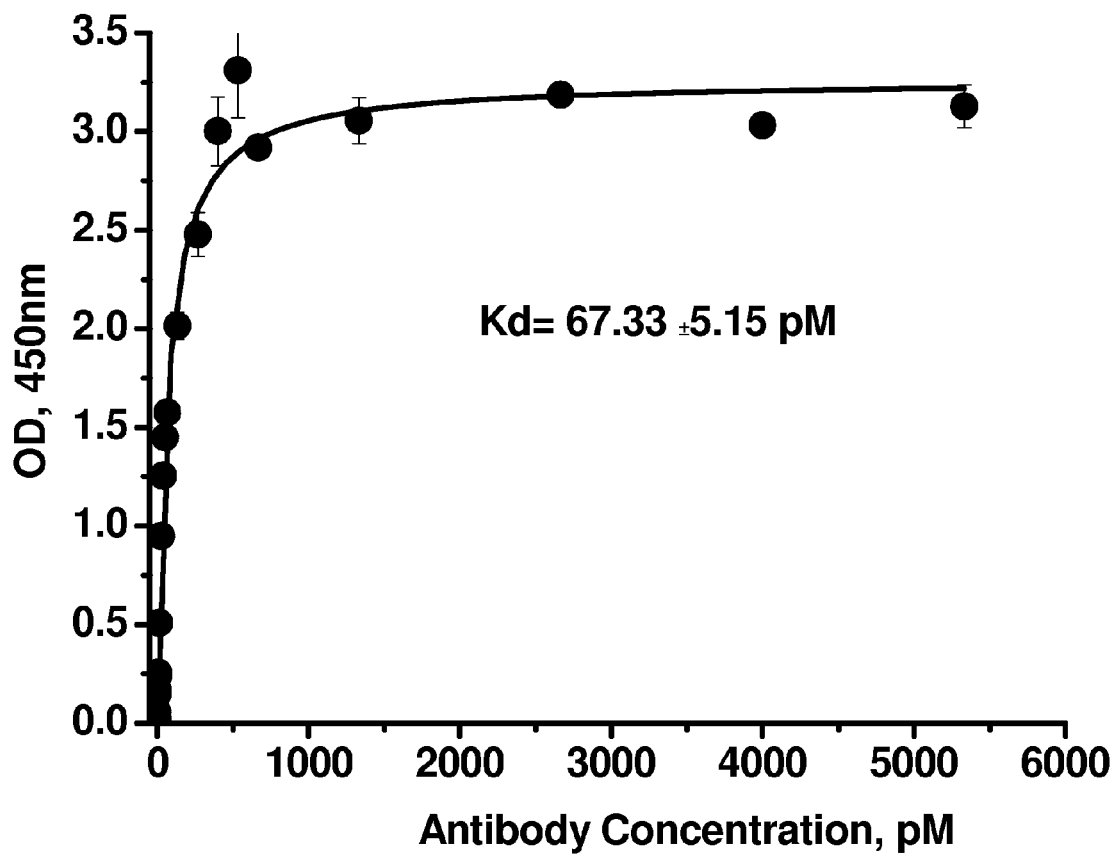
FIG. 3 illustrates the binding affinity of humanized anti-Bb antibody to Bb protein.

Standard terminologies including those used by skilled in the art are common and standard and have been used throughout the application without reservation.

The following definitions are provided in order to provide clarity with respect to the terms as they are used in the specification and claims, in order to describe the present invention.

As used herein, the term "alternative pathway" refers to complement activation, which has traditionally been thought to arise from proteolytic generation of C3b from complement factor C3, for example, by zymosan from fungal and yeast cell walls, lipopolysaccharide (LPS) from Gram-negative outer membranes, and rabbit erythrocytes, as well as from many pure polysaccharides, rabbit erythrocytes, viruses, bacteria, animal tumor cells, parasites and damaged cells.

As used herein, the term "antibody" encompasses antibodies and antibody fragments, which specifically bind to Bb or its polypeptides or portions, in which the antibody is derived from any antibody-producing mammal (e.g., a mouse, a rat, a rabbit, or a primate, including a human). Exemplary antibodies include polyclonal, monoclonal and recombinant antibodies; multi-specific antibodies (e.g., bi-specific antibodies), humanized antibodies; murine antibodies, chimeric (i.e. mouse-human, mouse-primate, primate-human), monoclonal antibodies, and anti-idiotype antibodies, as well as de-immunized antibodies, and may be any intact molecule or fragment thereof.

As used herein, the term "antibody fragment" refers to a portion derived from or related to a full-length anti-factor Bb antibody, generally including the antigen binding or variable region thereof. Illustrative examples of antibody fragments include Fab, Fab', F(ab)$_2$, F(ab')$_2$ and Fv fragments, scFv fragments, diabodies, linear antibodies, single-chain antibody molecules and multispecific antibodies formed from antibody fragments.

As used herein, the term "Bb inhibitory agent" refers to any agent that binds to or interacts with Bb and effectively inhibits Bb-dependent complement activation, including anti-Bb antibodies and Bb binding fragments thereof, natural and synthetic peptides. Bb inhibitory agents useful in the method of the invention may reduce Bb-dependent complement activation, therefore all activation, by greater than 20%. In one embodiment, the Bb inhibitory agent reduces complement activation by greater than 90%.

As used herein, a "chimeric antibody" is a recombinant protein that contains the variable domains and complementarily-determining regions derived from a non-human species (e.g., rodent) antibody, while the remainder of the antibody molecule is derived from a human antibody.

As used herein, the term "classical pathway" refers to both (1) complement activation of the C1-complex triggered by an antibody bound to a foreign particle and requires binding of the recognition molecule C1q, and also to (2) complement activation that occurs via antigen-antibody complex formation.

As used herein, a "humanized antibody" is a chimeric antibody that comprises a minimal sequence conforming to specific complementarily-determining regions derived from non-human immunoglobulin that is transplanted into a human antibody framework. Humanized antibodies are typically recombinant proteins in which only the antibody complementarily-determining regions are of non-human origin.

As used herein, the "membrane attack complex" ("MAC") refers to a complex of the five terminal complement components ($C_5$-$C_9$) that inserts into and disrupts membranes. MAC can also be referred to as C5b-9, and SC5b-9.

As used herein, "a subject" includes all mammals, including, but not limited to, dogs, cats, horses, sheep, goats, cows, rabbits, pigs, humans, non-human primates, and rodents. The alternative pathway can also provide an amplification loop for complement activation initially triggered via the classical and lectin pathways, in addition to its widely accepted role as an independent pathway for complement activation.

As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding.

The antibodies of the present invention are chimeric and humanized anti Bb monoclonal antibodies (mAb), and antigen binding fragments for the treatment of human diseases. The antibody of the present invention will provide high affinity antibodies useful to meet this need. The anti-Bb monoclonal antibody of this invention neutralizes the catalytic activity of Bb in a PC3bBb complex and protects the Factor D cleavage site on Factor B in PC3bB complex.

Both animal and plant derived anti-Bb monoclonal antibodies with characteristic CDR(s) that binds and inhibits Bb binding to the PC3bB complex are covered under the present invention. CDRs having greater than 60% homology between CDRs of the antibody of the present invention are covered under the present invention. A mouse monoclonal antibody used to generate the chimeric and humanized anti-Bb antibody is covered under the present invention.

The antibody of the present invention differs from the prior art in that this antibody a) does not inhibit the binding of Factor B to C3b, b) binds the factor D cleavage site on factor B, c) has no affect on the classical complement pathway, and d); binds Bb with 1:1 molar equivalence.

The humanized and murine anti-Bb antibodies inhibits the lysis of rabbits erythrocytes in sera from normal and disease.

The humanized and murine anti-Bb antibodies inhibit the production of C3a, C5a, C5b-9 and TNF alpha. These antibodies were generated against Bb and therefore do not cross react with Ba which is a fragment of the intact Ba molecule.

The antibodies of the present invention inhibit the formation of new C3b, PC3b, PC3bB, and PC3bBb. These antibodies exclusively inhibit the alternative pathway without having an effect on the amplification loop on the classical pathway.

Anti-factor Bb antibodies can be selected based on their ability to neutralize the Bb generated by the activation of the alternative pathway. The molar equivalence of 1:1 dictates that all of Bb is neutralized by the anti-Bb antibody.

Antibodies of the present invention have no effect on classical pathway activation. Thus, the monoclonal antibodies of the present invention do not inhibit the classical pathway. Inhibition of alternative pathway (amplification loop) should affect the classical pathway but these antibodies do not show any effect on the classical pathway activation even in situation where both pathways are generally activated.

Another aspect of the invention relates to antibodies that comprise the heavy chain and light chain CDR1s, CDR2s and CDR3s of mAb, or combinations thereof. The amino acid sequences of the variable heavy chain CDR 1, 2 and 3 regions are shown in SEQ ID NO's: 14, 16, and 18, respectively. The amino acid sequences of the variable light chain CDR 1, 2 and 3 regions are shown in SEQ ID NO's: 21, 23, and 25, respectively wherein the antibody specifically binds human Bb and B.

The antibody can be, for example, a chimeric antibody, humanized antibody, human antibody, a humanized antibody or a chimeric antibody The CDRs within the variable region may range from 90% similar to about 99% similar.

The antibodies of the present invention, the CDRs of the present invention, and the framework of the present invention are listed in FIGS. 12-17.

The antibodies of the present invention can be used to inhibit complement activation via the alternative pathway in vivo in subjects, including humans, suffering from an acute or chronic pathological injury. The present invention can be used in conjunction with the following diseases, disorders, injuries, and treatments, including but not limited to:

Extracorporeal circulation diseases and disorders: Post-cardiopulmonary bypass inflammation, post-operative pulmonary dysfunction, cardiopulmonary bypass, hemodialysis, leukopheresis, plasmapheresis, plateletpheresis, heparin-induced extracorporeal LDL precipitation (HELP), postperfusion syndrome, extracorporeal membrane oxygenation (ECMO), cardiopulmonary bypass (CPB), post-perfusion syndrome, systemic inflammatory response, and multiple organ failure.

Cardiovascular diseases and disorders: acute coronary syndromes, Kawaski disease (arteritis), Takayasu's arteritis, Henoch-Schonlein purpura nephritis, vascular leakage syndrome, percutaneous coronary intervention (PCI), myocardial infarction, ischemia-reperfusion injury following acute myocardial infarction, atherosclerosis, vasculitis, immune complex vasculitis, vasculitis associated with rheumatoid arthritis (also called malignant rheumatoid arthritis), systemic lupus erythematosus-associated vasculitis, sepsis, arteritis, aneurysm, cardiomyopathy, dilated cardiomyopathy, cardiac surgery, peripheral vascular conditions, renovascular conditions, cardiovascular conditions, cerebrovascular conditions, mesenteric/enteric vascular conditions, diabetic angiopathy, venous gas embolus (VGE), Wegener's granulomatosis, heparin-induced extracorporeal membrane oxygenation, and Behcet's syndrome.

Bone/Musculoskeletal diseases and disorders: arthritis, inflammatory arthritis, non-inflammatory arthritis, rheumatoid arthritis, juvenile rheumatoid arthritis, systemic juvenile rheumatoid arthritis, osteoarthritis, osteoporosis, systemic lupus erythematosus (SLE), Behcet's syndrome, and Sjogren's syndrome.

Transplantation diseases and disorders: transplant rejection, xenograft rejection, graft versus host disease, xenotransplantation of organs or grafts, allotransplantation of organs or grafts, and hyperacute rejection.

Eye/Ocular diseases and disorders: wet and dry age-related macular degeneration (AMD), choroidal neurovascularization (CNV), retinal damage, diabetic retinopathy, diabetic retinal microangiopathy, histoplasmosis of the eye, uveitis, diabetic macular edema, diabetic retinopathy, diabetic retinal microangiopathy, pathological myopia, central retinal vein occlusion (CRVO), corneal neovascularization, retinal neovascularization, retinal pigment epithelium (RPE), histoplasmosis of the eye, and Purtscher's retinopathy.

Hemolytic/Blood diseases and disorders: sepsis, systemic inflammatory response syndrome" (SIRS), hemorrhagic shock, acute respiratory distress syndrome (ARDS), catastrophic anti-phospholipid syndrome (CAPS), cold agglutinin disease (CAD), autoimmune thrombotic thrombocytopenic purpura (TTP), endotoxemia, hemolytic uremic syndrome (HUS), atypical hemolytic uremic syndrome (aHUS), paroxysmal nocturnal hemoglobinuria (PNH), sepsis, septic shock, sickle cell anemia, hemolytic anemia, hypereosinophilic syndrome, and anti-phospholipid syndrome (APLS).

Respiratory/Pulmonary diseases and disorders: asthma, Wegener's granulomatosis, transfusion-related acute lung injury (TRALI), antiglomerular basement membrane disease (Goodpasture's disease), eosinophilic pneumonia, hypersensitivity pneumonia, allergic bronchitis bronchiecstasis, reactive airway disease syndrome, respiratory syncytial virus (RSV) infection, parainfluenza virus infection, rhinovirus infection, adenovirus infection, allergic bronchopulmonary aspergillosis (ABPA), tuberculosis, parasitic lung disease, adult respiratory distress syndrome, chronic obstructive pulmonary disease (COPD), sarcoidosis, emphysema, bronchitis, cystic fibrosis, interstitial lung disease, acute respiratory distress syndrome (ARDS), transfusion-related acute lung injury, ischemia/reperfusion acute lung injury, byssinosis, heparin-induced extracorporeal membrane oxygenation, anaphylactic shock, and asbestos-induced inflammation.

Central and Peripheral Nervous System/Neurological diseases and disorders: multiple sclerosis (MS), myasthenia gravis (MG), myasthenia gravis, multiple sclerosis, Guillain Bane syndrome, Miller-Fisher syndrome, stroke, reperfusion following stroke, Alzheimer's disease, multifocal motor neuropathy (MMN), demyelination, Huntington's disease, amyotrophic lateral sclerosis (ALS), Parkinson's disease, degenerative disc disease (DDD), meningitis, cranial nerve damage from meningitis, variant Creutzfeldt-Jakob Disease (vCJD), idiopathic polyneuropathy, brain/cerebral trauma (including, but not limited to, hemorrhage, inflammation, and edema), and neuropathic pain.

Trauma-induced injuries and disorders: hemorrhagic shock, hypovolemic shock, spinal cord injury, neuronal injury, cerebral trauma, cerebral ischemia reperfusion, crush injury, wound healing, severe burns, and frostbite.

Renal diseases and disorders: renal reperfusion injury, poststreptococcal glomerulonephritis (PSGN), Goodpasture's disease, membranous nephritis, Berger's Disease/IgA nephropathy, mesangioproliferative glomerulonephritis, membranous glomerulonephritis, membranoproliferative glomerulonephritis (mesangiocapillary glomerulonephritis), acute postinfectious glomerulonephritis, cryoglobulinemic glomerulonephritis, lupus nephritis, Henoch-Schonlein purpura nephritis, and renal cortical necrosis (RCN).

Reperfusion injuries and disorders of organs: including but not limited to heart, brain, kidney, and liver.

Reproduction and urogenital diseases and disorders: painful bladder diseases and disorders, sensory bladder diseases and disorders, spontaneous abortion, male and female diseases from infertility, diseases from pregnancy, fetomaternal tolerance, pre-eclampsia, urogenital inflammatory diseases, diseases and disorders from placental dysfunction, diseases and disorders from miscarriage, chronic abacterial cystitis, and interstitial cystitis.

Skin/Dermatologic diseases and disorders: burn injuries, psoriasis, atopic dermatitis (AD), eosinophilic spongiosis, urticaria, thermal injuries, pemphigoid, epidermolysis bullosa acquisita, autoimmune bullous dermatoses, bullous pemphigoid, scleroderma, angioedema, hereditary angioneurotic edema (HAE), erythema multiforme, herpes gestationis, Sjogren's syndrome, dermatomyositis, and dermatitis herpetiformis.

Gastrointestinal diseases and disorders: Crohn's disease, Celiac Disease/gluten-sensitive enteropathy, Whipple's disease, intestinal ischemia, inflammatory bowel disease, and ulcerative colitis.

Endocrine diseases and disorders: Hashimoto's thyroiditis, juvenile lymphocytic thyroiditis, stress anxiety, and other diseases affecting prolactin, growth or insulin-like growth factor, adrenocorticotropin release, pancreatitis, Addison's disease, diabetic conditions including, but not limited to, type 1 and type 2 diabetes, type I diabetes mellitus, sarcoidosis, diabetic retinal microangiopathy, non-obese diabetes (IDDM), angiopathy, neuropathy or retinopathy complications of IDDM or Type-2 diabetes, and insulin resistance.

Treatment of Malignancies: diseases and disorders arising from chemotherapeutics and radiation therapy.

The antibodies of the present invention can be therapeutic. Murine, chimeric, humanized, and primatized antibodies are currently considered therapeutic. However with recent advances in science, the antibody can also be replaced by other types of antibodies in which the interaction of the antibody like molecule may fall within the range of low pMole to high pMole to low nMole.

Both the chimeric antibodies and the humanized antibodies have human framework constant regions. The framework regions of the humanized and human are either natural human framework regions or the altered human framework regions in order to increase the affinity and efficacy of the said CDR regions. Constant regions may or may not be present in the said antibody. Various methods are available to produce antibodies with and without the constant regions in plants, bacterial and mammalian cell system.

Functional activity of the anti-Bb antibody is defined as the ability of the anti-Bb antibody to inhibit only AP activation without affecting the amplification loop of the classical pathway. These antibodies (1) inhibit to the catalytic activity of the PC3bB complex, (2) reduce PC3bBb formation and/or C3bBb formation, (3) reduce concentration of free C3b, (4) reduce formation of C3b, (5) reduce formation of C3a, C5a and C5b-9, (6) reduces monocytes CD11b expression, (7) reduces neutrophil CD11b expression, (8) reduces platelet CD62 P expression, (9) reduces leukocyte-platelet conjugate formation, (10) reduces tumor necrosis factor alpha (TNF), and (11) reduces neutrophil elastase formation.

Bispecific antibodies can be generated that can comprise (i) two antibodies one with a specificity to Bb and another to a second molecule that are conjugated together, (ii) a single antibody that has one chain specific to Bb and a second chain specific to a second molecule, or (iii) a single chain antibody that has specificity to Bb and the other molecule. Such bi-specific antibodies can be generated using techniques that are well known in the art.

The anti-Bb antibody or fragments thereof can be used in therapeutic methods for the prophylactic and therapeutic treatment of diseases mediated, directly or indirectly, by a component of the alternative complement pathway, and/or by a factor generated following activation of the alternative complement pathway.

The present invention also provides methods of inhibiting the adverse effects of alternative pathway derived Bb-dependent complement activation. The Bb inhibitory agents can be used alone as a primary therapy or in combination with other methods as complement to enhance the benefits of other treatments.

The inhibitory agents can be small molecules, aptamers, DNA fragments, small peptides representing CDR domains, SiRNA. These inhibitory agents inhibit PC3bBb binding to C3, C5, C9, and C5b-9.

The Bb inhibitory agent can be administered in various ways by intra-arterial, intracranial, intravenous, subcutaneous, intramuscular, or other parenteral administration. Potentially orally for non-peptidergic inhibitors, and most suitably by intra-arterial or intravenous administration. Administration may be repeated periodically as determined by a physician for optimal therapeutic effect.

EXAMPLES

Unless stated otherwise, all reagents were of high grade available. All complement proteins, alternative and classical pathway buffers, detection antibodies, and erythrocytes were from Complement Technologies (Tyler, Tex.) or Quidel Corporation (San Diego, Calif.). Flow cytometry antibodies were from BD Biosciences, San Jose, Calif.TMB substrate was from Kirkegaard & Perry Limited, Gathersburg, Md. All secondary antibodies were from American Qualex, San Clemente, Calif., BSA and other reagents were all from Sigma-Aldrich, St Louise, Mo.

ELISA plate readers (SpectraMax® 190 and 250) were from Molecular Devices, and Flow Cytometer was FACS-Calibur™ Varity 3D program was used for data analyses, Curve fittings were done using MicroCal Origin® program. Hemolysis kinetic assay was run using SpectraMax®, Molecular Devices., ELISA plates were from Corning Costar, Lowell, Mass.

Humanized and chimeric antibodies contain the CDRs of the parent murine monoclonal antibody, sequence (SEQ ID No 1 and SEQ ID No 2), which is present in this application. Mice were injected with human Bb (Complement Technology, Tyler, Tex.) and mouse serum was screened for Bb binding and AP inhibitory activity. Spleen cells from properdin positive mouse were fused with myeloma cells using standard procedures. The fusion cells were cloned into a single cell population using limiting dilution technique. The cells in 96 well plate were allowed to grow to supernatant was tested using properdin binding and alternative pathway inhibition. Cells that block AP activation were identified and further screened using those that inhibit C5b-9 formation. These clones were categorized under 1D3 which inhibit erythrocyte lysis. The antibody secreting cell line was sequenced to generate an amino acid sequence shown in SEQ ID NO: 1 and SEQ ID NO:2. The CDRs from both heavy and light chains were grafted in the human framework to generate various humanized antibody sequences SEQ ID NO: 3 through SEQ ID NO: 12. The antibody from SEQ ID NO 9 through 12 were produced in mammalian CHO cells, expressed, secreted and purified to produce a full IgG1k. The antibody was characterized as shown below.

Example 1

Humanized Anti-Bb Antibody Binds Factor B and Bb Proteins with High Affinity

Figure 4:
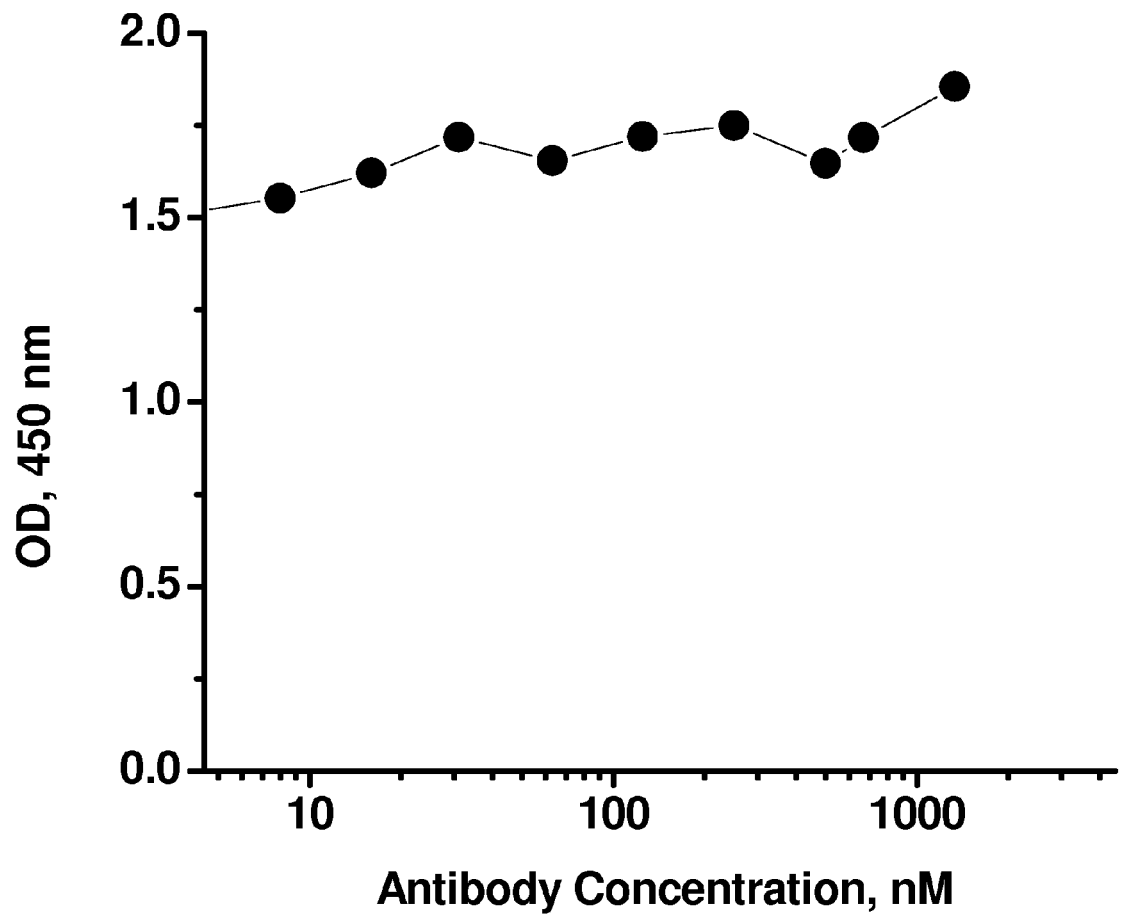
FIG. 4 illustrates the humanized anti-Bb antibody does not inhibit Factor B binding to C3b.

The affinity of anti-Bb IgG1 and its antigen binding fragments to human factor B and Bb is in the range of low pM Antibody. Antibody binding to Bb neutralizes the catalytic activity of the PC3bBb (C3/C5 convertase). Binding of anti-Bb to human factor B blocks the factor D cleavage site on factor B. To perform these experiments, polystyrene microtiter plates were coated with human factor B and Bb (2.0 μg/50 μl per well) in phosphate buffered saline (PBS) overnight at 4° C. After aspirating the properdin solution, the wells were blocked with PBS containing 1% bovine serum albumin (BSA) (Sigma-Aldrich, St. Louis, Mo.) for 1 hour at room temperature. Wells without peptide or properdin coating served as background controls. Aliquots of humanized anti-factor Bb were added to the B and Bb coated wells and allowed to incubate for 1 hour to allow binding to occur. Following a 1 hour incubation period at room temperature, the plate was rinsed with PBS five times and incubated with 1:2000 diluted detection peroxidase-conjugated goat anti-human monoclonal antibody. Following this incubation, the plate was rinsed and the bound peroxidase was identified using TMB reagent.

As shown in FIGS. 2 and 3, humanized anti-Bb binds factor B (FIG. 2) and Bb (FIG. 3) with picomolar affinity.

Example 2

Humanized Anti-Bb Monoclonal Antibody does not Inhibit Factor B Binding to C3b Anti-factor B antibodies of previous inventions have typically inhibited B interaction with C3b. This novel antibody does not inhibit the binding of Factor B to C3b. In a typical experiment, polystyrene microtiter plate wells (96-well medium binding plates, Corning Costar, Cambridge, Mass.) were coated with C3b (2 μg/50 μl/well, Complement Technology, Tyler, Tex.) in phosphate-buffered saline (PBS) pH 7.4 overnight at 4° C. After aspirating the C3b solution, wells are blocked with PBS containing 1% bovine serum albumin (BSA; Sigma Chemical) for 1 h at room temperature. Wells without C3b coating serve as the background controls. Aliquots of humanized anti-Bb were added to solution containing the fixed concentration of Factor B. Following 1 h incubation at room temperature, the wells are extensively rinsed with PBS. The total bound "B" was detected with the polyclonal anti-B antibody. None of the humanized anti-Bb concentrations inhibited the binding of factor B to C3b, as shown in FIG. 4.

Example 3

Humanized Anti-Factor Bb Inhibits the Formation of C3/C5 Convertase (PC3bBb) of Alternative Complement Pathway Alternative complement pathway is activated in normal human serum by lipopolysaccharide from Salmonella Typhosa. We have utilized this paradigm to demonstrate whether anti-properdin antibody of this invention would inhibit the formation of PC3bBb. We measured the deposition of P, C3b, Bb, and C5b-9 in the presence and absence the humanized anti-Bb antibody. The deposited P, C3b, Bb, and C5b-9 were detected with appropriate antibodies. In the presence of humanized anti-Bb antibodies, a dose dependent inhibition of C3 and C5 convertase formation was noticed as indicated by the inhibition of deposition of each of the P, C3b, Bb, and C5b-9 molecules.

In a typical assay, polystyrene microtiter plate wells were coated with LPS (Lipopolysaccharide from Salmonella Typhosa) at 2 µg/50 µl in PBS overnight. The wells were incubated with 1% BSA in PBS to block the unoccupied sites in the wells. Following a 2-hour blocking at room temperature and rinsing with PBS, normal human serum (10%) in an AP buffer was mixed with varying concentrations of the antibody and fragments. The mixture was incubated onto LPS coated wells. The plate was incubated for 2 hours at 37° C. to allow complement AP activation to occur. Following incubation, the plates were extensively washed with PBS, and components of the C3 convertase were detected with the appropriate antibodies. We detected C3b with rabbit anti-human C3c at 1:2000 in blocking solution, goat anti-human P at 1:2000 in blocking solution and goat anti-human factor Bb at 1:500 in blocking solution and HRPO conjugated anti-human C5b-9 at 1:2000 in blocking solution. Plates were incubated with their respective antibodies for 1-hour at room temperature. Following the incubation, the plates were rinsed with PBS and the bound antibodies were detected with peroxidase labeled goat anti-rabbit at 1:2000 for C3b and peroxidase labeled rabbit anti-goat at 1:2000 in blocking solution for P detection. All plates were developed with TMB following extensive washing with PBS. The blue color was quenched with 1 M orthophosphoric acid. The presence of C3b, P and Bb and MAC together are indicative of C3/C5 convertase formation.

Figure 5:
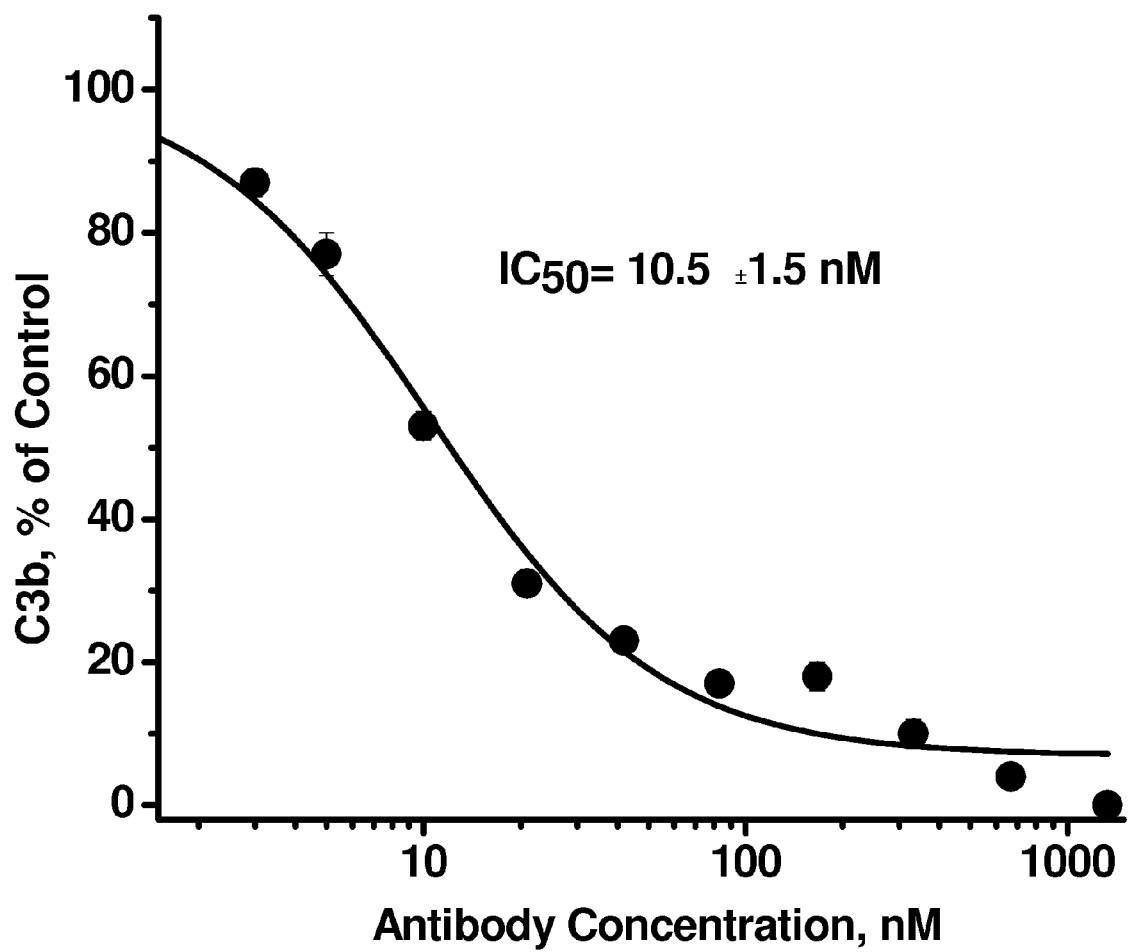
FIG. 5 illustrates that the humanized anti-Bb inhibits the formation of new C3b molecules that form the new C3/C5 convertase
Figure 6:
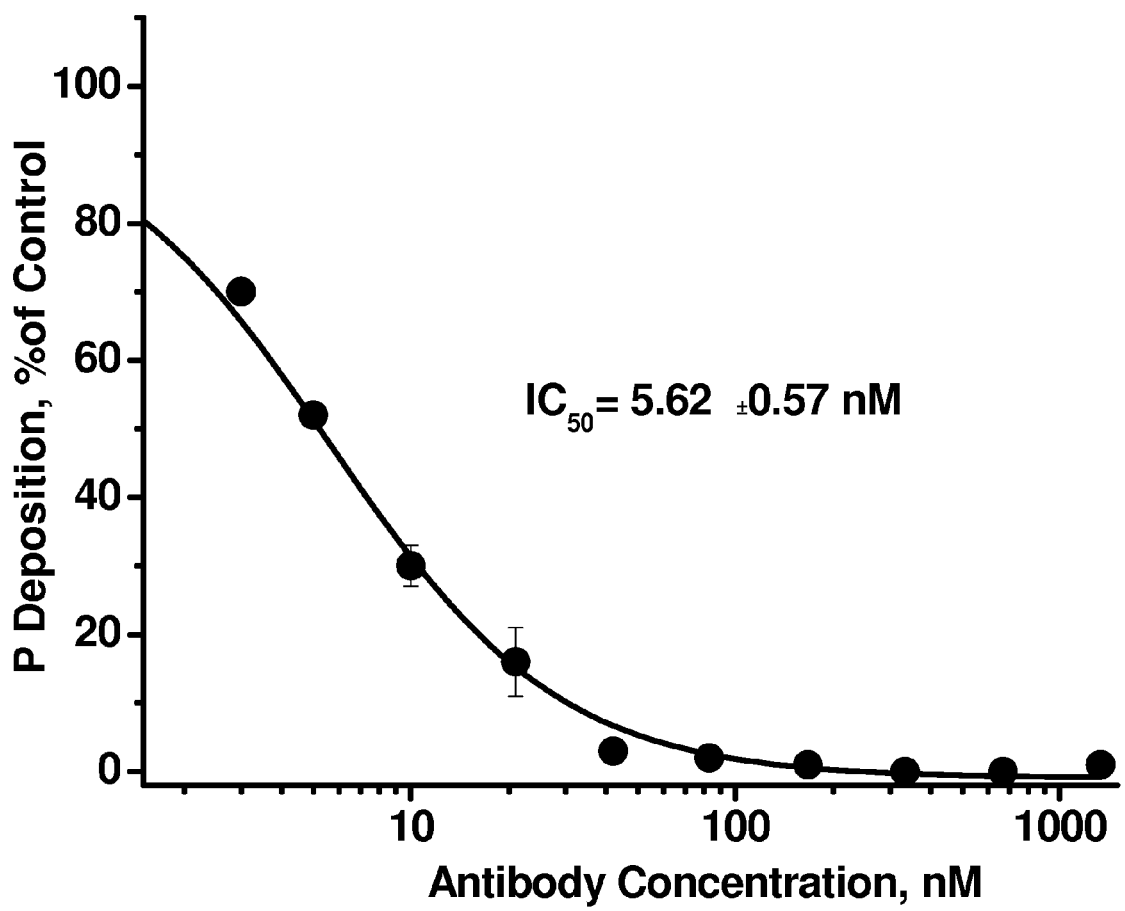
FIG. 6 illustrates that the humanized anti-Bb inhibits the formation of new PC3b complex.
Figure 7:
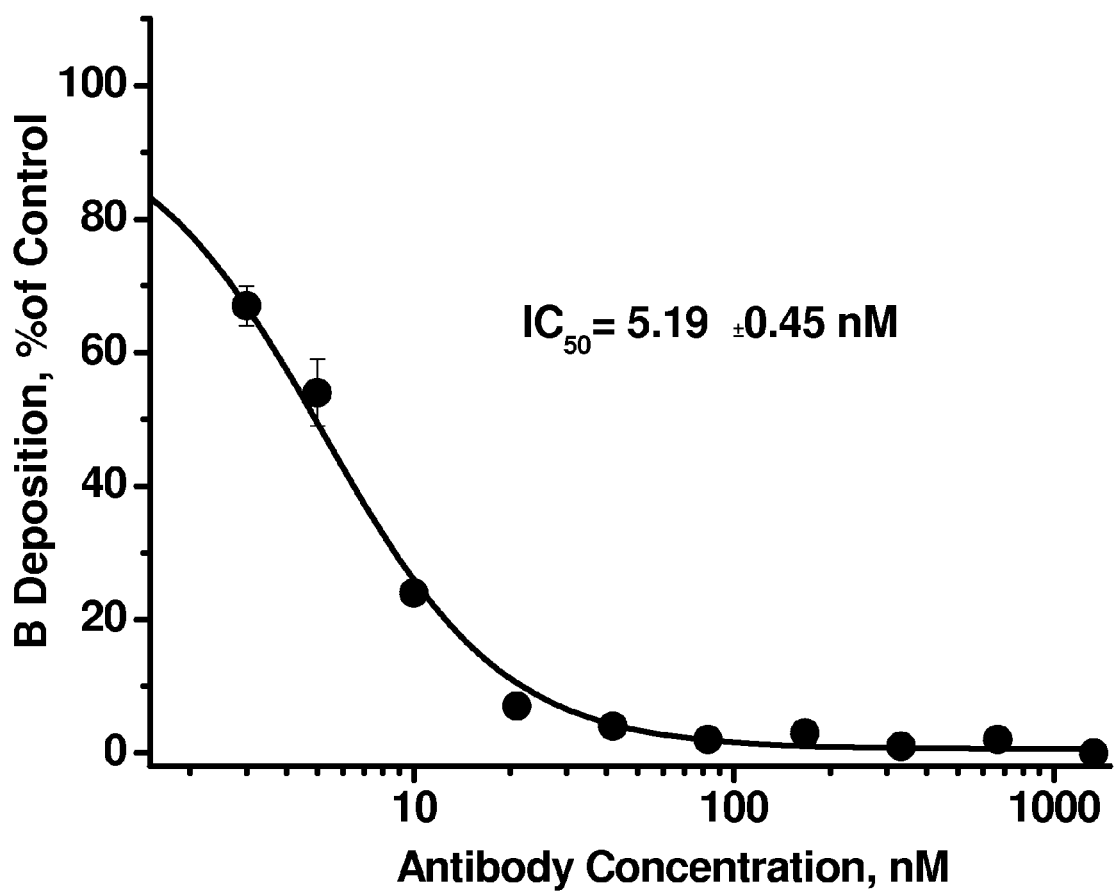
FIG. 7 illustrates that the humanized anti-Bb inhibits the formation of new factor B/Bb molecules that are associated with C3/C5 convertase.
Figure 8:
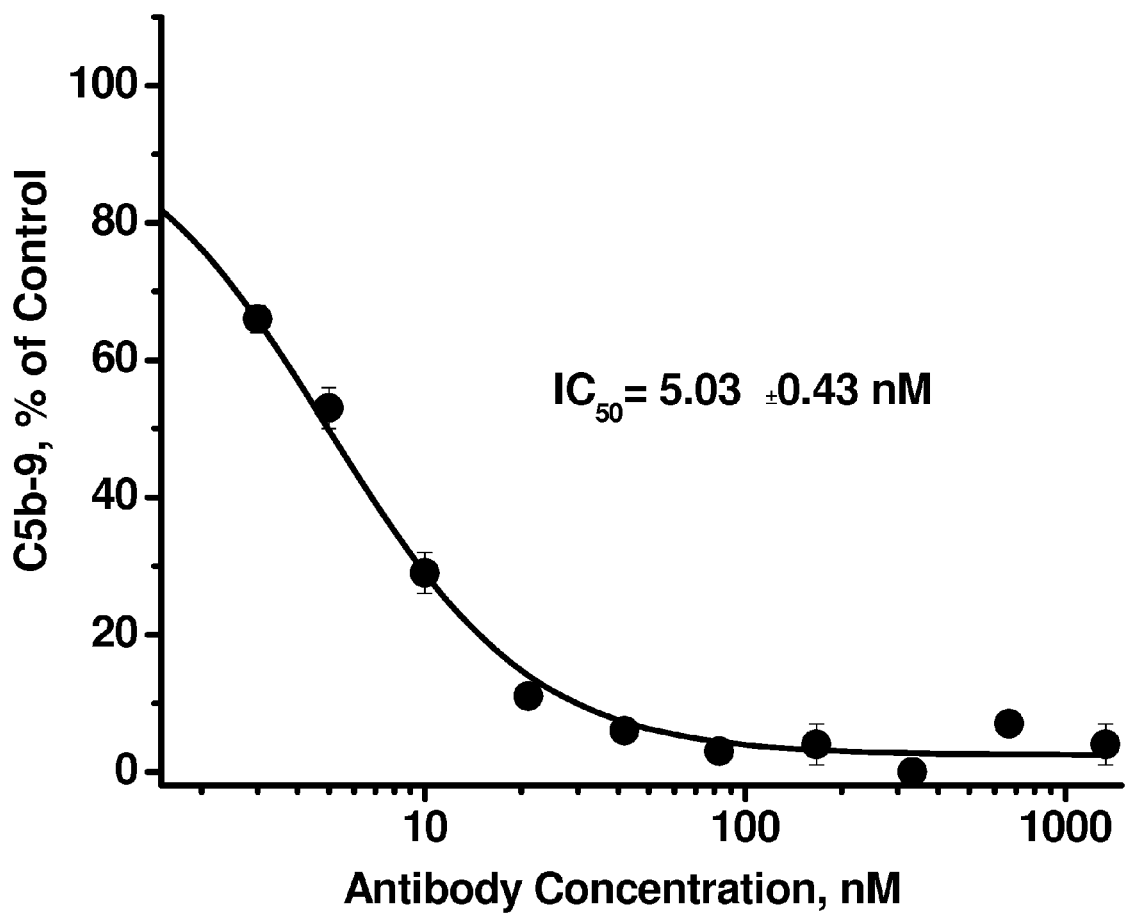
FIG. 8 illustrates that humanized anti-Bb inhibits the formation of C5b-9 formation required for erythrocyte lysis and tissue injury.

FIG. 5 shows a dose dependent inhibition of C3b deposition, FIG. 6 shows a dose dependent deposition of P deposition, FIG. 7 shows a dose dependent deposition of Bb formation, and FIG. 8 shows a dose dependent deposition of C5b-9 deposition by humanized anti-Bb antibodies. These data provide direct evidence that anti-Bb monoclonal antibodies prevent convertase formation and inhibit AP activation.

Example 4

Humanized Anti-Bb Antibody Inhibits Alternative Pathway (AP) Dependent Lysis of Rabbit Red Blood Cell (rRBC)

This erythrocyte lysis assay is based on the formation of terminal complement complex on the surface of the rRBC. As a result, the rRBCs are lysed. The progressive decrease in light scatter at 700 nm is a direct measure of erythrocyte lysis. Typically, rRBC(s) are incubated in normal human serum in gelatin veronal buffer containing 5 mM $MgCl_2$. Under these conditions, the surface of rRBC triggers the activation of alternative pathway in normal human serum. The alternative pathway activation leads to the formation of C5b-9 complex on the surface of the rRBC(s). Agents that inhibit the formation of C5b-9 complexes are expected to inhibit cellular lysis. To evaluate the effect of anti-properdin antibody and fragments thereof, various concentrations of IgG, F(ab')$_2$, and Fab were incubated with normal human serum (10% NHS) in AP buffer at 37° C. with a fixed concentration of rabbit erythrocytes in a temperature controlled ELISA plate reader capable of reading at 700 nm. A progressive decrease in light scatter (due to lysis of intact cells) was measured at 700 nm as a function of time. The data were recorded and analyzed with a SpectraMax® 190 plate reader and SoftMax® software. For calculation total inhibition was calculated at each concentration of the IgG, F(ab')2, and Fab, and the results were expressed as a % of unlysed controls. Data at each concentration was plotted in a sigmoidal plot with MicroCal Origin® Software.

Figure 9:
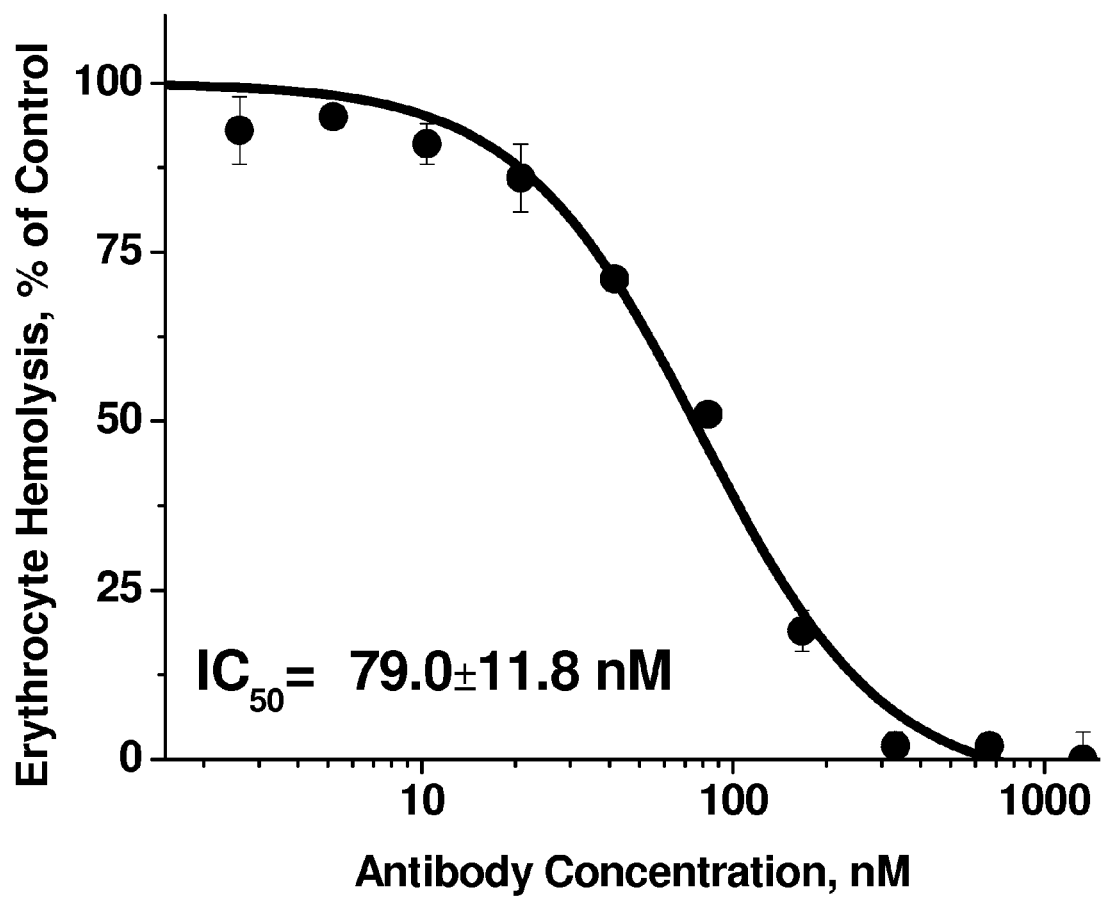
FIG. 9 illustrates that humanized anti-Bb antibody inhibits the alternative pathway dependent lysis of erythrocytes.

As shown in FIG. 9, Humanized anti-Bb IgG inhibits AP dependent hemolysis of rRBC in normal human serum with an $IC_{50}$ of 79 nM in normal human serum inhibiting erythrocyte lysis. The antibodies are able to inhibit lysis with an $IC_{50}$ of approximately 79 nM.

Figure 11:
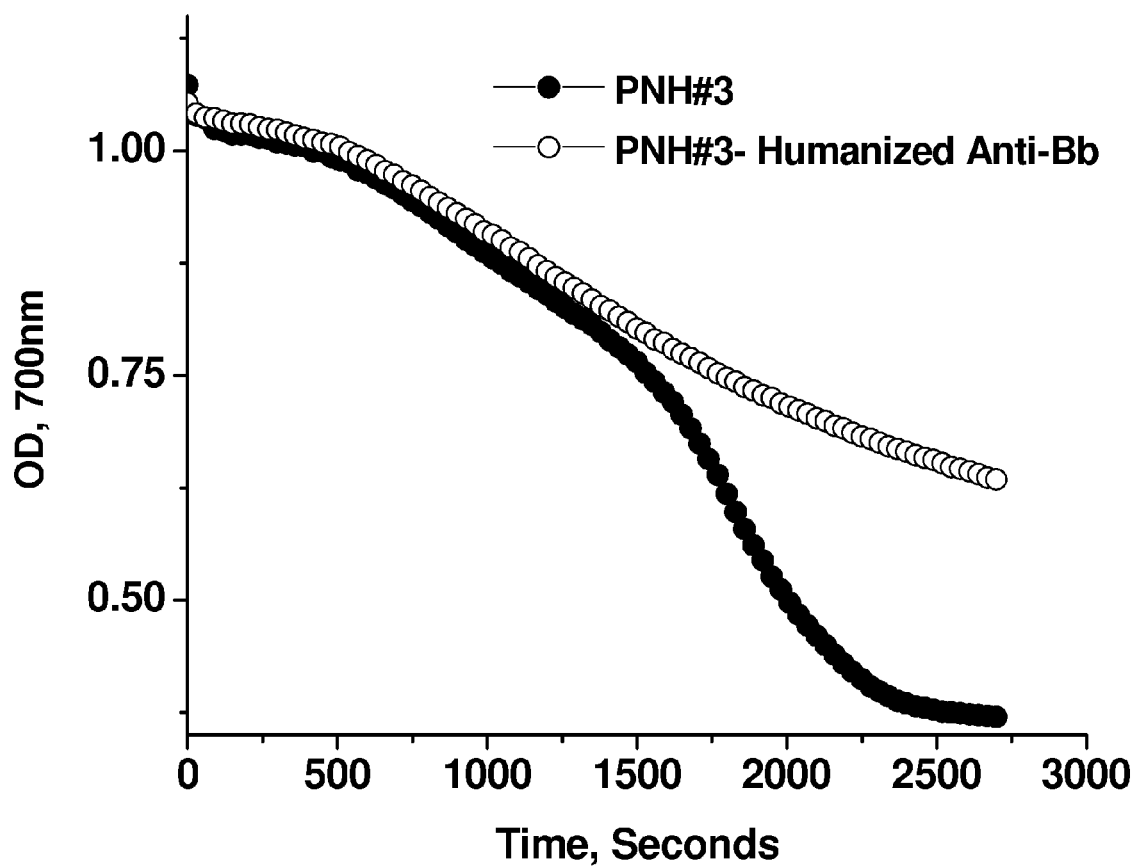
FIG. 11 illustrates that humanized antibody inhibits lysis of rabbit erythrocytes in PNH serum.

Similar experiment was conducted with serum from Paroxysmal Nocturnal Hemoglobinuria (PNH) patients. Instead of 10% final serum concentration, we used 40% final serum concentration. As shown in FIG. 11, Humanized anti-Bb prevented the lysis of erythrocytes in PNH serum.

Example 5

Humanized Anti-Bb does not Inhibit the Classical Pathway Activation

Monoclonal antibodies of the present invention do not inhibit the classical pathway which is required for host defense. Antibody sensitized sheep erythrocytes were incubated with 10% normal human serum in gelatin veronal buffer containing calcium (5 mM $CaCl_2/MgCl_2$) buffer. Antibody sensitized sheep cells activate the classical pathway. As a result, C5b-9 is formed on the surface of the erythrocyte acused lysis. We tested 10% normal human serum. Under both conditions, Anti-Bb did not inhibit sheep erythrocyte lysis. In a typical assay, 100 µl of antibody sensitized sheep erythrocytes (Complement Technologies, Tyler, Tex.) were incubated in 10% normal human serum in CP buffer to allow complement activation to occur. As a result of CP activation, erythrocytes undergo lysis. The progressive decrease in light scattering due to cellular lysis was measured at 700 nm as a function of time.

Figure 10:
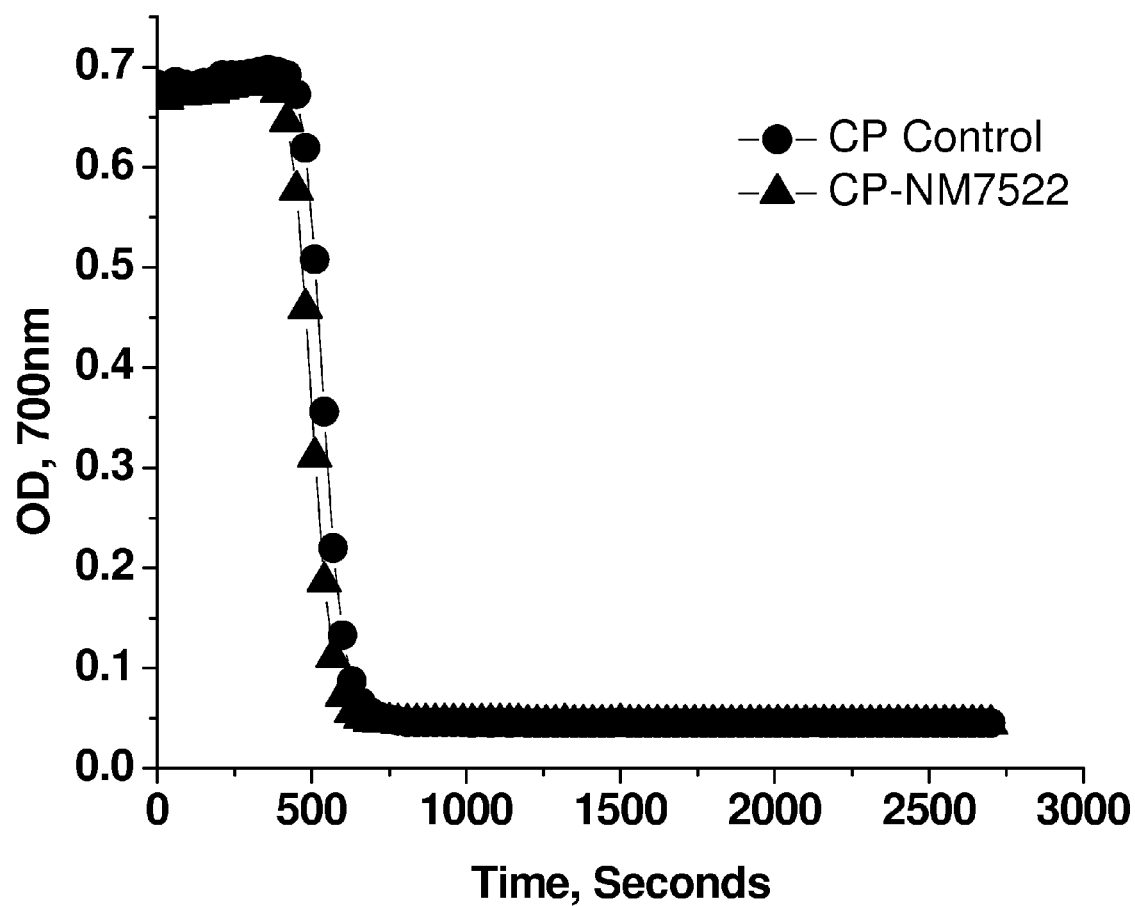
FIG. 10 illustrates that humanized anti-Bb antibody does not inhibit the classical pathway activation.

As shown in FIG. 10, humanized anti-Bb IgG does not inhibit the lysis of the antibody sensitized sheep cells normal human serum. These results suggest that anti-Bb antibodies are capable of selectively inhibiting the alternative complement pathway without affecting the classical pathway activation.

Example 6

Production of Humanized Anti-Bb Antibodies

Murine monoclonal antibody harboring the CDRs were sequenced and CDRs were grafted within various human framework regions. The antibody was cloned and expressed in CHO cells using methods developed in the art. FIGS. 12 through 17 show antibody CDR and framework regions.

Example 7

Epitope Mapping of the Bb Protein

The epitope mapping of the Bb protein was conducted by Pepscan using clips technology. Multiple overlapping peptides were synthesized and antibody was allowed to bind the peptides at 1 μg/ml concentration. Peptides that produced the strongest signal were identified to be the potential epitopes for the antibody. Sequences 47 & 48 were identified for one antibody clone whereas sequences 49, 50, and 51 were identified for the humanized anti-Bb antibody.

The invention claimed is:

1. An isolated anti-Bb antibody or portion thereof comprising a heavy chain variable domain including 3 CDRs having amino acid sequences of SEQ ID NO: 14, SEQ ID NO: 16, and SEQ ID NO: 18 and a light chain variable domain including 3 CDRs having amino acid sequences of SEQ ID NO: 21, SEQ ID NO: 23, and SEQ ID NO: 25.

2. The anti-Bb antibody or portion thereof of claim 1, comprising humanized frame work regions, wherein the humanized framework regions are selected from SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

3. The anti-Bb antibody or portion thereof of claim 1, comprising humanized or non-natural framework regions, wherein the humanized or non-natural framework regions are selected from SEQ ID NO: 13, SEQ ID NO: 15, SEQ ID NO: 17, SEQ ID NO: 19, SEQ ID NO: 20, SEQ ID NO: 22, SEQ ID NO: 24, and SEQ ID NO: 26.

4. The anti-Bb antibody or portion thereof of claim 1, comprising humanized or non-natural framework regions, wherein the humanized or non-natural framework regions are selected from SEQ ID NO: 27, SEQ ID NO: 28, SEQ ID NO: 29, SEQ ID NO: 19, SEQ ID NO: 20, SEQ ID NO: 22, SEQ ID NO: 30, and SEQ ID NO: 26.

5. The anti-Bb antibody or portion thereof of claim 1, comprising humanized or non-natural framework regions, wherein the humanized or non-natural framework regions are selected from SEQ ID NO: 31, SEQ ID NO: 32, SEQ ID NO: 33, SEQ ID NO: 19, SEQ ID NO: 20, SEQ ID NO: 34, SEQ ID NO: 35, and SEQ ID NO: 26.

6. The anti-Bb antibody or portion thereof of claim 1, comprising humanized or non-natural framework regions, wherein the humanized or non-natural framework regions are selected from SEQ ID NO: 43, SEQ ID NO: 44, SEQ ID NO: 45, SEQ ID NO: 19, SEQ ID NO: 46, SEQ ID NO: 40, SEQ ID NO: 41, and SEQ ID NO: 42.

7. The anti-Bb antibody or portion thereof of claim 1, wherein the anti-Bb antibody or portion thereof binds to peptide regions located on factor Bb having an amino acid sequence selected from the group consisting of SEQ ID NO: 47, SEQ ID NO: 48, SEQ ID NO: 49, SEQ ID NO: 50, and SEQ ID NO: 51.

8. The anti-Bb antibody or portion thereof of claim 1, wherein the antibody or portion thereof antibody inhibits the formation of C3b via the inhibition of the formation of the PC3bBb complex.

9. The anti-Bb antibody or portion thereof of claim 1, wherein the antibody or portion thereof inhibits the formation of newly produced C3a, C5a, SC5b-9.

10. The anti-Bb antibody or portion thereof of claim 1, wherein the antibody or portion thereof inhibits the activation of neutrophil, monocytes, and platelets.

11. The anti-Bb antibody or portion thereof of claim 1, wherein the antibody or portion thereof, inhibits the lysis of erythrocytes.

12. A pharmaceutical composition comprising a therapeutically effective amount of an anti-Bb antibody or portion thereof of claim 1.

13. A method of treating a disorder wherein complement activation contributes to the disorder pathology in a subject in need thereof, comprising: administering a therapeutically effective amount of an anti-Bb antibody or portion thereof that includes a heavy chain variable domain including 3 CDRs having amino acid sequences of SEQ ID NO: 14, SEQ ID NO: 16, and SEQ ID NO: 18 and a light chain variable domain including 3 CDRs having amino acid sequences of SEQ ID NO: 21, SEQ ID NO: 23, and SEQ ID NO: 25.

14. The method of claim 13, wherein the disorder is an inflammatory disorder or an autoimmune disease.

15. The method of claim 13, wherein the disorder is an ocular disorder.

16. The method of claim 15, wherein the ocular disorder is selected from the group consisting of wet and dry age related macular degeneration, choroidal neovascularization, uveitis, diabetic retinopathy, diabetic macular edema, pathological myopia, Von Hippel-Lindau disease, diabetic retinopathy, histoplasmosis of the eye, diabetic retinopathy, choroidal neovascularization (CNV), Central Retinal Vein Occlusion (CRVO), corneal neovascularization, geographic atrophy, drusen disease, and retinal neovascularization.

17. The method of claim 13, wherein the disorder is selected from the group consisting of asthma, chronic obstructive pulmonary disease ("COPD"), allergic bronchopulmonary aspergillosis, hypersensitivity pneumonia, eosinophilic pneumonia, emphysema, bronchitis, allergic bronchitis bronchiecstasis, cyctic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus ("RSV") infection, parainfluenza virus ("PIV") infection, rhinovirus ("RV") infection, and adenovirus infection.

* * * * *

```
                         SEQUENCE LISTING

<160> NUMBER OF SEQ ID NOS: 51

<210> SEQ ID NO 1
<211> LENGTH: 121
<212> TYPE: PRT
<213> ORGANISM: Mus musculus

<400> SEQUENCE: 1

Gln Val Gln Leu Gln Gln Ser Gly Ala Glu Leu Ala Lys Pro Gly Ala
1               5                   10                  15

Ser Val Arg Met Ser Cys Lys Ala Ser Gly Tyr Thr Phe Thr Asn Tyr
            20                  25                  30

Trp Ile His Trp Val Lys Gln Arg Pro Gly Gln Gly Leu Glu Trp Ile
        35                  40                  45

Gly Tyr Ile Asn Pro Asn Thr Gly Tyr Asn Asp Tyr Asn Gln Lys Phe
    50                  55                  60

Lys Asp Lys Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Tyr Cys
                85                  90                  95

Ala Arg Gly Gly Gln Leu Gly Leu Arg Arg Ala Met Asp Tyr Trp Gly
            100                 105                 110

Gln Gly Thr Ser Val Thr Val Ser Ser
            115                 120

<210> SEQ ID NO 2
<211> LENGTH: 113
<212> TYPE: PRT
<213> ORGANISM: Mus musculus

<400> SEQUENCE: 2

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Asp Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asp Glu Tyr Pro Trp
                85                  90                  95

Thr Phe Gly Gly Gly Thr Lys Leu Glu Ile Lys Arg Ala Asp Ala Ala
            100                 105                 110

Pro

<210> SEQ ID NO 3
<211> LENGTH: 121
<212> TYPE: PRT
<213> ORGANISM: Homo sapiens
```

-continued

<400> SEQUENCE: 3

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Asn Tyr
            20                  25                  30

Trp Ile His Trp Ile Arg Gln Ser Pro Ser Arg Gly Leu Glu Trp Leu
        35                  40                  45

Gly Tyr Ile Asn Pro Asn Thr Gly Tyr Asn Asp Tyr Asn Gln Lys Phe
    50                  55                  60

Lys Asp Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Gln Leu Gly Leu Arg Arg Ala Met Asp Tyr Trp Gly
            100                 105                 110

Gln Gly Thr Leu Val Thr Val Ser Ser
        115                 120

<210> SEQ ID NO 4
<211> LENGTH: 111
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Asp Glu Tyr Pro Trp
                85                  90                  95

Thr Phe Gly Gln Gly Thr Lys Val Glu Ile Lys Arg Thr Val Ala
            100                 105                 110

<210> SEQ ID NO 5
<211> LENGTH: 121
<212> TYPE: PRT
<213> ORGANISM: Homo sapiens

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Tyr Thr Phe Thr Asn Tyr
            20                  25                  30

Trp Ile His Trp Val Arg Gln Ala Pro Gly Lys Gly Leu Glu Trp Val
        35                  40                  45

Ser Tyr Ile Asn Pro Asn Thr Gly Tyr Asn Asp Tyr Asn Gln Lys Phe
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

```
                    85                  90                  95

Ala Lys Gly Gly Gln Leu Gly Leu Arg Arg Ala Met Asp Tyr Trp Gly
            100                 105                 110

Gln Gly Thr Leu Val Thr Val Ser Ser
            115                 120

<210> SEQ ID NO 6
<211> LENGTH: 111
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Asp Glu Tyr Pro Trp
                85                  90                  95

Thr Phe Gly Gln Gly Thr Lys Val Glu Ile Lys Arg Thr Val Ala
            100                 105                 110

<210> SEQ ID NO 7
<211> LENGTH: 121
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Trp Ile His Trp Val Arg Gln Ala Pro Gly Lys Gly Leu Glu Trp Val
        35                  40                  45

Gly Tyr Ile Asn Pro Asn Thr Gly Tyr Asn Asp Tyr Asn Gln Lys Phe
    50                  55                  60

Lys Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Gly Gly Gln Leu Gly Leu Arg Arg Ala Met Asp Tyr Trp Gly
            100                 105                 110

Gln Gly Thr Leu Val Thr Val Ser Ser
            115                 120

<210> SEQ ID NO 8
<211> LENGTH: 111
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Lys Ser Ile Ser Lys Tyr
            20                  25                  30

Leu Ala Trp Tyr Gln Lys Pro Gly Lys Ala Pro Lys Val Leu Ile
        35                  40                  45

Tyr Ser Gly Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Glu Tyr Pro Trp
                85                  90                  95

Thr Phe Gly Gln Gly Thr Lys Val Glu Ile Lys Arg Thr Val Ala
            100                 105                 110

<210> SEQ ID NO 9
<211> LENGTH: 121
<212> TYPE: PRT
<213> ORGANISM: Homo sapiens

<400> SEQUENCE: 9

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Ile
        35                  40                  45

Gly Tyr Ile Asn Pro Asn Thr Gly Tyr Asn Asp Tyr Asn Gln Lys Phe
 50                  55                  60

Lys Asp Arg Ala Thr Leu Thr Ala Asp Lys Ser Ser Ser Thr Val Tyr
65                  70                  75                  80

Met Gln Leu Ser Ser Leu Arg Ser Glu Asp Thr Ala Val Tyr Tyr Cys
                85                  90                  95

Ala Arg Gly Gly Gln Leu Gly Leu Arg Arg Ala Met Asp Tyr Trp Gly
            100                 105                 110

Gln Gly Thr Leu Val Thr Val Ser Ser
        115                 120

<210> SEQ ID NO 10
<211> LENGTH: 107
<212> TYPE: PRT
<213> ORGANISM: Homo sapiens

<400> SEQUENCE: 10

Asp Val Gln Ile Thr Gln Ser Pro Ser Thr Leu Ser Ala Ser Pro Gly
1               5                   10                  15

Asp Arg Ile Thr Ile Thr Cys Arg Ala Ser Lys Ser Ile Ser Lys Tyr
            20                  25                  30

Leu Ala Trp Tyr Gln Asp Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Met Tyr Tyr Cys Gln Gln His Asp Glu Tyr Pro Trp
                85                  90                  95

Thr Phe Gly Gln Gly Thr Lys Leu Glu Ile Lys
            100                 105

<210> SEQ ID NO 11
<211> LENGTH: 121
<212> TYPE: PRT
<213> ORGANISM: Homo sapiens

<400> SEQUENCE: 11

Gln Val Gln Leu Val Gln Ser Gly Ala Glu Ala Lys Pro Gly Ala
1               5                   10                  15

Ser Val Lys Met Ser Cys Lys Ala Ser Gly Tyr Thr Phe Thr Asn Tyr
                20                  25                  30

Trp Ile His Trp Val Lys Gln Arg Pro Gly Gln Gly Leu Glu Trp Ile
            35                  40                  45

Gly Tyr Ile Asn Pro Asn Thr Gly Tyr Asn Asp Tyr Asn Gln Lys Phe
    50                  55                  60

Lys Asp Lys Ala Thr Leu Thr Ala Asp Lys Ser Ser Thr Val Tyr
65                  70                  75                  80

Met Gln Leu Ser Ser Leu Thr Ser Glu Asp Thr Ala Val Tyr Tyr Cys
                85                  90                  95

Ala Arg Gly Gly Gln Leu Gly Leu Arg Arg Ala Met Asp Tyr Trp Gly
            100                 105                 110

Gln Gly Thr Leu Val Thr Val Ser Ser
        115                 120

<210> SEQ ID NO 12
<211> LENGTH: 107
<212> TYPE: PRT
<213> ORGANISM: Homo sapiens

<400> SEQUENCE: 12

Asp Val Gln Ile Thr Gln Ser Pro Ser Tyr Leu Ser Ala Ser Pro Gly
1               5                   10                  15

Asp Thr Ile Thr Ile Thr Cys Arg Ala Ser Lys Ser Ile Ser Lys Tyr
                20                  25                  30

Leu Ala Trp Tyr Gln Asp Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Met Tyr Tyr Cys Gln Gln His Asp Glu Tyr Pro Trp
                85                  90                  95

Thr Phe Gly Gln Gly Thr Lys Leu Glu Ile Lys
            100                 105

<210> SEQ ID NO 13
<211> LENGTH: 25
<212> TYPE: PRT
<213> ORGANISM: Homo sapiens

<400> SEQUENCE: 13

Glu Val Gln Leu Val Gln Ser Gly Ala Glu Val Lys Lys Pro Gly Glu
1               5                   10                  15

Ser Leu Arg Ile Ser Cys Lys Gly Ser
                20                  25

<210> SEQ ID NO 14
<211> LENGTH: 10

```
<212> TYPE: PRT
<213> ORGANISM: Homo sapiens

<400> SEQUENCE: 14

Gly Tyr Thr Phe Thr Asn Tyr Trp Ile His
1               5                   10

<210> SEQ ID NO 15
<211> LENGTH: 14
<212> TYPE: PRT
<213> ORGANISM: Homo sapiens

<400> SEQUENCE: 15

Trp Ile Arg Gln Ser Pro Ser Arg Gly Leu Glu Trp Leu Gly
1               5                   10

<210> SEQ ID NO 16
<211> LENGTH: 17
<212> TYPE: PRT
<213> ORGANISM: Homo sapiens

<400> SEQUENCE: 16

Tyr Ile Asn Pro Asn Thr Gly Tyr Asn Asp Tyr Asn Gln Lys Phe Lys
1               5                   10                  15

Asp

<210> SEQ ID NO 17
<211> LENGTH: 32
<212> TYPE: PRT
<213> ORGANISM: Homo sapiens

<400> SEQUENCE: 17

Arg Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

<210> SEQ ID NO 18
<211> LENGTH: 12
<212> TYPE: PRT
<213> ORGANISM: Homo sapiens

<400> SEQUENCE: 18

Gly Gly Gln Leu Gly Leu Arg Arg Ala Met Asp Tyr
1               5                   10

<210> SEQ ID NO 19
<211> LENGTH: 11
<212> TYPE: PRT
<213> ORGANISM: Homo sapiens

<400> SEQUENCE: 19

Trp Gly Gln Gly Thr Leu Val Thr Val Ser Ser
1               5                   10

<210> SEQ ID NO 20
<211> LENGTH: 23
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
1               5                   10                  15
```

```
Asp Arg Val Thr Ile Thr Cys
            20
```

<210> SEQ ID NO 21
<211> LENGTH: 11
<212> TYPE: PRT
<213> ORGANISM: Homo sapiens

<400> SEQUENCE: 21

```
Arg Ala Ser Lys Ser Ile Ser Lys Tyr Leu Ala
1               5                   10
```

<210> SEQ ID NO 22
<211> LENGTH: 15
<212> TYPE: PRT
<213> ORGANISM: Homo sapiens

<400> SEQUENCE: 22

```
Trp Tyr Gln Gln Lys Pro Gly Lys Ala Pro Lys Leu Leu Ile Tyr
1               5                   10                  15
```

<210> SEQ ID NO 23
<211> LENGTH: 7
<212> TYPE: PRT
<213> ORGANISM: Homo sapiens

<400> SEQUENCE: 23

```
Ser Gly Ser Thr Leu Gln Ser
1               5
```

<210> SEQ ID NO 24
<211> LENGTH: 32
<212> TYPE: PRT
<213> ORGANISM: Homo sapiens

<400> SEQUENCE: 24

```
Gly Val Pro Ser Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30
```

<210> SEQ ID NO 25
<211> LENGTH: 9
<212> TYPE: PRT
<213> ORGANISM: Homo sapiens

<400> SEQUENCE: 25

```
Gln Gln His Asp Glu Tyr Pro Trp Thr
1               5
```

<210> SEQ ID NO 26
<211> LENGTH: 14
<212> TYPE: PRT
<213> ORGANISM: Homo sapiens

<400> SEQUENCE: 26

```
Phe Gly Gln Gly Thr Lys Val Glu Ile Lys Arg Thr Val Ala
1               5                   10
```

<210> SEQ ID NO 27
<211> LENGTH: 25
<212> TYPE: PRT
<213> ORGANISM: Homo sapiens

<400> SEQUENCE: 27

```
Glu Val Gln Leu Val Glu Ser Gly Gly Gly Leu Val Gln Pro Gly Arg
1               5                   10                  15

Ser Leu Arg Leu Ser Cys Ala Ala Ser
            20                  25

<210> SEQ ID NO 28
<211> LENGTH: 14
<212> TYPE: PRT
<213> ORGANISM: Homo sapiens

<400> SEQUENCE: 28

Trp Val Arg Gln Ala Pro Gly Lys Gly Leu Glu Trp Val Ser
1               5                   10

<210> SEQ ID NO 29
<211> LENGTH: 32
<212> TYPE: PRT
<213> ORGANISM: Homo sapiens

<400> SEQUENCE: 29

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 30
<211> LENGTH: 32
<212> TYPE: PRT
<213> ORGANISM: Homo sapiens

<400> SEQUENCE: 30

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 31
<211> LENGTH: 25
<212> TYPE: PRT
<213> ORGANISM: Homo sapiens

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 32
<211> LENGTH: 14
<212> TYPE: PRT
<213> ORGANISM: Homo sapiens

<400> SEQUENCE: 32

Trp Val Arg Gln Ala Pro Gly Lys Gly Leu Glu Trp Val Gly
1               5                   10

<210> SEQ ID NO 33
<211> LENGTH: 32
<212> TYPE: PRT
<213> ORGANISM: Homo sapiens

<400> SEQUENCE: 33
```

```
Arg Phe Thr Phe Ser Leu Asp Thr Ser Lys Ser Thr Ala Tyr Leu Gln
1               5                   10                  15

Met Asn Ser Leu Arg Ala Glu Asp Thr Ala Val Tyr Tyr Cys Ala Lys
            20                  25                  30
```

<210> SEQ ID NO 34
<211> LENGTH: 15
<212> TYPE: PRT
<213> ORGANISM: Homo sapiens

<400> SEQUENCE: 34

```
Trp Tyr Gln Gln Lys Pro Gly Lys Ala Pro Lys Val Leu Ile Tyr
1               5                   10                  15
```

<210> SEQ ID NO 35
<211> LENGTH: 32
<212> TYPE: PRT
<213> ORGANISM: Homo sapiens

<400> SEQUENCE: 35

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 36
<211> LENGTH: 25
<212> TYPE: PRT
<213> ORGANISM: Homo sapiens

<400> SEQUENCE: 36

```
Gln Val Gln Leu Val Gln Ser Gly Ala Glu Val Lys Lys Pro Gly Ala
1               5                   10                  15

Ser Val Lys Met Ser Cys Lys Ala Ser
            20                  25
```

<210> SEQ ID NO 37
<211> LENGTH: 14
<212> TYPE: PRT
<213> ORGANISM: Homo sapiens

<400> SEQUENCE: 37

```
Trp Val Arg Gln Ala Pro Gly Gln Gly Leu Glu Trp Ile Gly
1               5                   10
```

<210> SEQ ID NO 38
<211> LENGTH: 32
<212> TYPE: PRT
<213> ORGANISM: Homo sapiens

<400> SEQUENCE: 38

```
Arg Ala Thr Leu Thr Ala Asp Lys Ser Ser Thr Val Tyr Met Gln
1               5                   10                  15

Leu Ser Ser Leu Arg Ser Glu Asp Thr Ala Val Tyr Tyr Cys Ala Arg
            20                  25                  30
```

<210> SEQ ID NO 39
<211> LENGTH: 23
<212> TYPE: PRT
<213> ORGANISM: Homo sapiens

<400> SEQUENCE: 39

```
Asp Val Gln Ile Thr Gln Ser Pro Ser Thr Leu Ser Ala Ser Pro Gly
```

```
1               5                   10                  15
Asp Arg Ile Thr Ile Thr Cys
            20

<210> SEQ ID NO 40
<211> LENGTH: 15
<212> TYPE: PRT
<213> ORGANISM: Homo sapiens

<400> SEQUENCE: 40

Trp Tyr Gln Asp Lys Pro Gly Lys Thr Asn Lys Leu Leu Ile Tyr
1               5                   10                  15

<210> SEQ ID NO 41
<211> LENGTH: 32
<212> TYPE: PRT
<213> ORGANISM: Homo sapiens

<400> SEQUENCE: 41

Gly Ile Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Met Tyr Tyr Cys
            20                  25                  30

<210> SEQ ID NO 42
<211> LENGTH: 10
<212> TYPE: PRT
<213> ORGANISM: Homo sapiens

<400> SEQUENCE: 42

Phe Gly Gln Gly Thr Lys Leu Glu Ile Lys
1               5                   10

<210> SEQ ID NO 43
<211> LENGTH: 25
<212> TYPE: PRT
<213> ORGANISM: Homo sapiens

<400> SEQUENCE: 43

Gln Val Gln Leu Val Gln Ser Gly Ala Glu Val Ala Lys Pro Gly Ala
1               5                   10                  15

Ser Val Lys Met Ser Cys Lys Ala Ser
            20                  25

<210> SEQ ID NO 44
<211> LENGTH: 14
<212> TYPE: PRT
<213> ORGANISM: Homo sapiens

<400> SEQUENCE: 44

Trp Val Lys Gln Arg Pro Gly Gln Gly Leu Glu Trp Ile Gly
1               5                   10

<210> SEQ ID NO 45
<211> LENGTH: 32
<212> TYPE: PRT
<213> ORGANISM: Homo sapiens

<400> SEQUENCE: 45

Lys Ala Thr Leu Thr Ala Asp Lys Ser Ser Thr Val Tyr Met Gln
1               5                   10                  15

Leu Ser Ser Leu Thr Ser Glu Asp Thr Ala Val Tyr Tyr Cys Ala Arg
            20                  25                  30
```

<210> SEQ ID NO 46
<211> LENGTH: 23
<212> TYPE: PRT
<213> ORGANISM: Homo sapiens

<400> SEQUENCE: 46

Asp Val Gln Ile Thr Gln Ser Pro Ser Tyr Leu Ala Ser Pro Gly
1               5                   10                  15

Asp Thr Ile Thr Ile Thr Cys
            20

<210> SEQ ID NO 47
<211> LENGTH: 16
<212> TYPE: PRT
<213> ORGANISM: Homo sapiens

<400> SEQUENCE: 47

Tyr Ala Asp Pro Asn Thr Cys Arg Gly Asp Ser Gly Gly Pro Leu Ile
1               5                   10                  15

<210> SEQ ID NO 48
<211> LENGTH: 16
<212> TYPE: PRT
<213> ORGANISM: Homo sapiens

<400> SEQUENCE: 48

Val His Lys Arg Ser Arg Phe Ile Gln Val Gly Val Ile Ser Trp Gly
1               5                   10                  15

<210> SEQ ID NO 49
<211> LENGTH: 16
<212> TYPE: PRT
<213> ORGANISM: Homo sapiens

<400> SEQUENCE: 49

Val Trp Glu His Arg Lys Gly Thr Asp Tyr His Lys Gln Pro Trp Gln
1               5                   10                  15

<210> SEQ ID NO 50
<211> LENGTH: 16
<212> TYPE: PRT
<213> ORGANISM: Homo sapiens

<400> SEQUENCE: 50

Gly Ala Val Val Ser Glu Tyr Phe Val Leu Thr Ala Ala His Cys Phe
1               5                   10                  15

<210> SEQ ID NO 51
<211> LENGTH: 17
<212> TYPE: PRT
<213> ORGANISM: Homo sapiens

<400> SEQUENCE: 51

Lys Arg Asp Leu Glu Ile Glu Val Val Leu Phe His Pro Asn Tyr Asn
1               5                   10                  15

Ile